(12) United States Patent
Werner

(10) Patent No.: US 8,535,618 B1
(45) Date of Patent: Sep. 17, 2013

(54) TEST STRIP DISPENSER

(76) Inventor: Robert L. Werner, Columbia, SC (US)

( * ) Notice: Subject to any disclaimer, the term of this patent is extended or adjusted under 35 U.S.C. 154(b) by 0 days.

(21) Appl. No.: 13/199,714

(22) Filed: Sep. 7, 2011

Related U.S. Application Data

(60) Provisional application No. 61/380,889, filed on Sep. 8, 2010.

(51) Int. Cl.
*B01L 3/00* (2006.01)

(52) U.S. Cl.
USPC .............. 422/430; 422/547; 422/50; 422/63; 436/44; 436/808

(58) Field of Classification Search
USPC ................ 422/50, 63, 430, 547; 436/44, 808
See application file for complete search history.

(56) References Cited

U.S. PATENT DOCUMENTS

| | | |
|---|---|---|
| 1,986,658 A | 1/1935 | Witter |
| 2,483,609 A | 10/1949 | Barmore |
| 2,553,671 A | 5/1951 | O'Brien |
| 2,684,179 A | 7/1954 | Sachs |
| 2,812,106 A | 11/1957 | Rink |
| 2,813,659 A | 11/1957 | Christopher |
| 4,220,256 A | 9/1980 | Torri |
| 4,796,744 A | 1/1989 | Sanger |
| 5,097,938 A | 3/1992 | Gruner |
| 5,298,425 A | 3/1994 | Kuhn |
| 5,378,630 A | 1/1995 | Kai |
| 5,556,597 A | 9/1996 | Shindo |
| 5,720,924 A | 2/1998 | Eikmeier |
| 6,497,845 B1 | 12/2002 | Sacherer |
| 6,682,704 B2 | 1/2004 | Bottwein |
| 6,827,899 B2 * | 12/2004 | Maisey et al. ................. 422/430 |
| 6,872,358 B2 | 3/2005 | Hagen |
| 7,337,918 B2 | 3/2008 | Fowler |
| 7,455,451 B2 | 11/2008 | Pearl |
| 7,582,262 B2 | 9/2009 | Funke |
| 2003/0036200 A1 * | 2/2003 | Charlton ......................... 436/43 |
| 2004/0069793 A1 * | 4/2004 | Brown et al. .................... 221/30 |
| 2008/0217354 A1 | 9/2008 | Newman |
| 2011/0204079 A1 * | 8/2011 | Chan ............................. 221/232 |

* cited by examiner

Primary Examiner — Lyle Alexander
(74) Attorney, Agent, or Firm — J. Bennett Mullinax, LLC

(57) ABSTRACT

A test strip dispenser that has a housing that defines a dispensing opening is provided. A cylindrical body engages the housing and is capable of rotating about an axis to rotate relative to the housing. A test strip engages an outer surface of the cylindrical body and is carried by the cylindrical body about the axis. Alignment of the test strip with the dispensing opening causes the test strip to fall off of and out of engagement with the outer surface and through the dispensing opening.

19 Claims, 24 Drawing Sheets

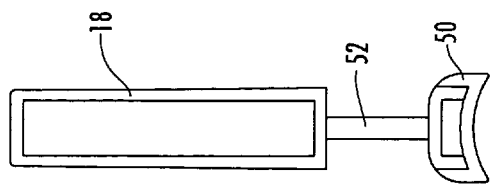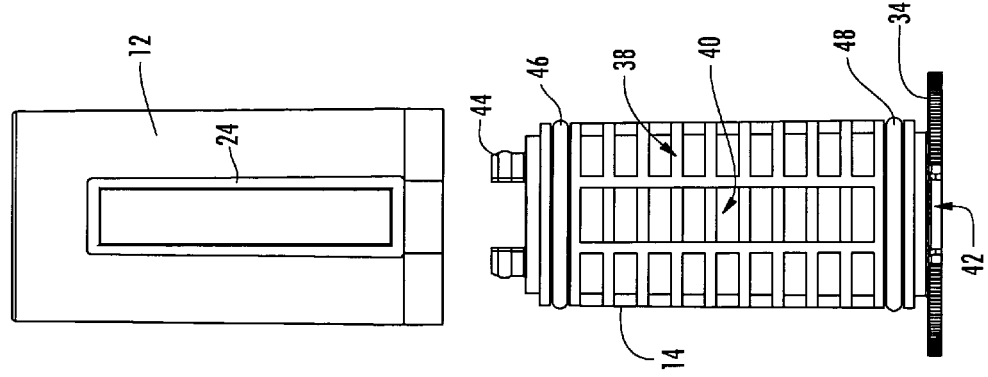
FIG. 17

TEST STRIP DISPENSER

CROSS REFERENCE TO RELATED APPLICATIONS

This application claims the benefit of U.S. Application Ser. No. 61/380,889 filed on Sep. 8, 2010 and entitled, "Test Strip Dispenser." U.S. Application Ser. No. 61/380,889 is incorporated by reference herein in its entirety for all purposes.

FIELD OF THE INVENTION

The present invention relates generally to a test strip dispenser. More particularly, the present application involves a test strip dispenser for dispensing blood glucose test strips that features a rotating cylindrical body that allows for a single test strip to be dispensed while protecting the non-dispensed test strips from contamination.

BACKGROUND

Test strips are often used to determine the amount of glucose or cholesterol present within the human body. Further, test strips are sometimes employed in other applications such as when a sanitizing solution for cleaning is used and whose potency is checked via the test strips. Generally, a test strip is constructed in a rectangular like manner having a width from 0.1-0.5 millimeters and a length of 3.5-4.0 millimeters. The test strips can have a thickness that is less than 0.1 millimeters and may have a slippery, plastic like surface. The user may apply a drop of blood onto the test strip to ascertain a glucose or cholesterol level when managing diabetes or monitoring cardiovascular conditions.

A user is typically provided with a plurality of test strips that are stored within a cylindrical, plastic container. At such time a test strip is desired, the user can open an end of the cylindrical container and turn the container upside down so that a test strip can be removed via gravity. Such an approach may be problematic in that additional test strips can spill out of the container and onto the ground thus becoming contaminated. The user will have to collect and return the test strips to the container again increasing the chances of contamination and increasing the time and effort needed in performing the testing method. As an alternative way of removing the test strip, the user may place one or two fingers into the cylindrical container in an attempt to grasp a single test strip amongst the plurality of test strips. However, this method may cause the user's finger to inadvertently contact a sensitive portion of the test strip thus contaminating the test strip and generating erroneous results. Users with impaired dexterity or visibility may have an even harder time in removing the desired test strip and may have an increased risk of contamination of the stored test strips. Still further, the constant opening and closing of the test strip container may result in the stored test strips being subjected to moisture, sunlight, and other contaminants that degrade the accuracy of the test strips.

Test strip dispensers are known for use in storing and dispensing a single test strip upon actuation. However, such test strip dispensers employ complicated mechanical linkages or require other additional components be provided in order to bias the test strips. Additional components and complexity increase the cost to the user and increase the odds of dispensing malfunction. As such, there remains room for variation and improvement within the art.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended Figs. in which:

FIG. 17 is an exploded assembly view of the test strip dispenser of FIG. 14 from a generally top facing angle of the dispenser.

Figure 1:
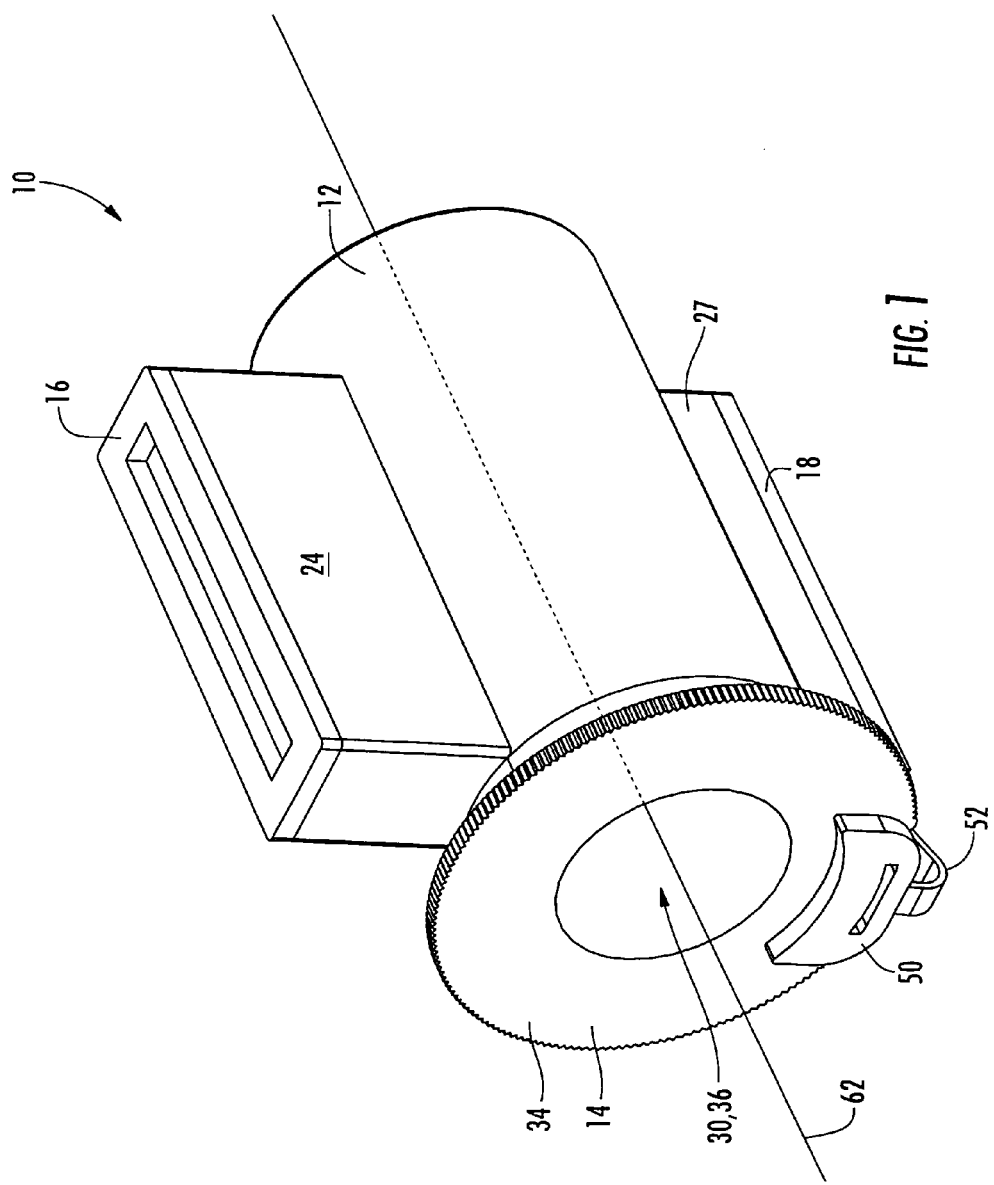
FIG. 1 is a perspective view of a test strip dispenser in accordance with one exemplary embodiment.
Figure 2:
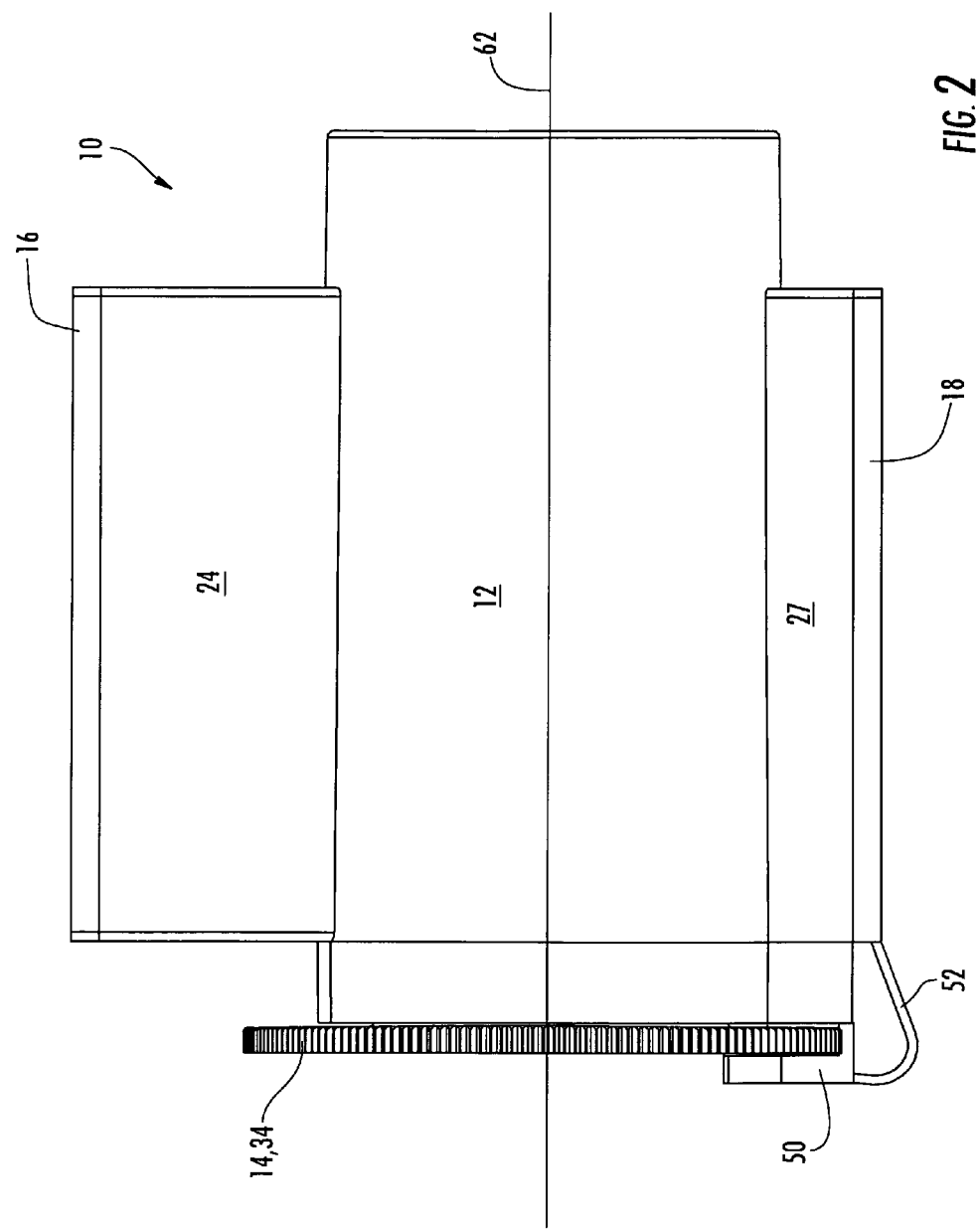
FIG. 2 is a side view of the test strip dispenser of FIG. 1.
Figure 3:
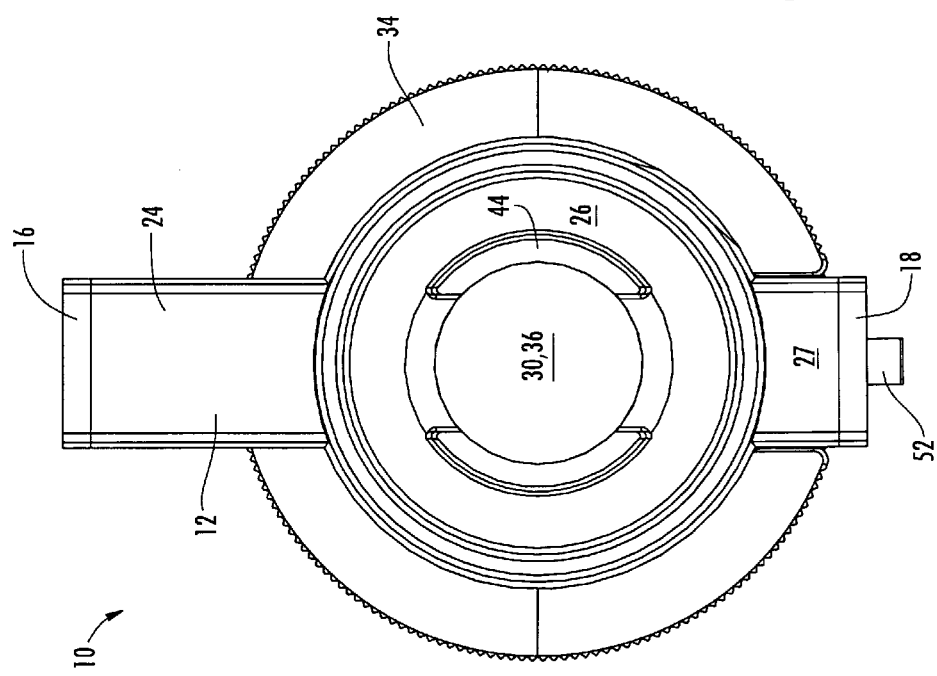
FIG. 3 is a back view of the test strip dispenser of FIG. 1.
Figure 4:
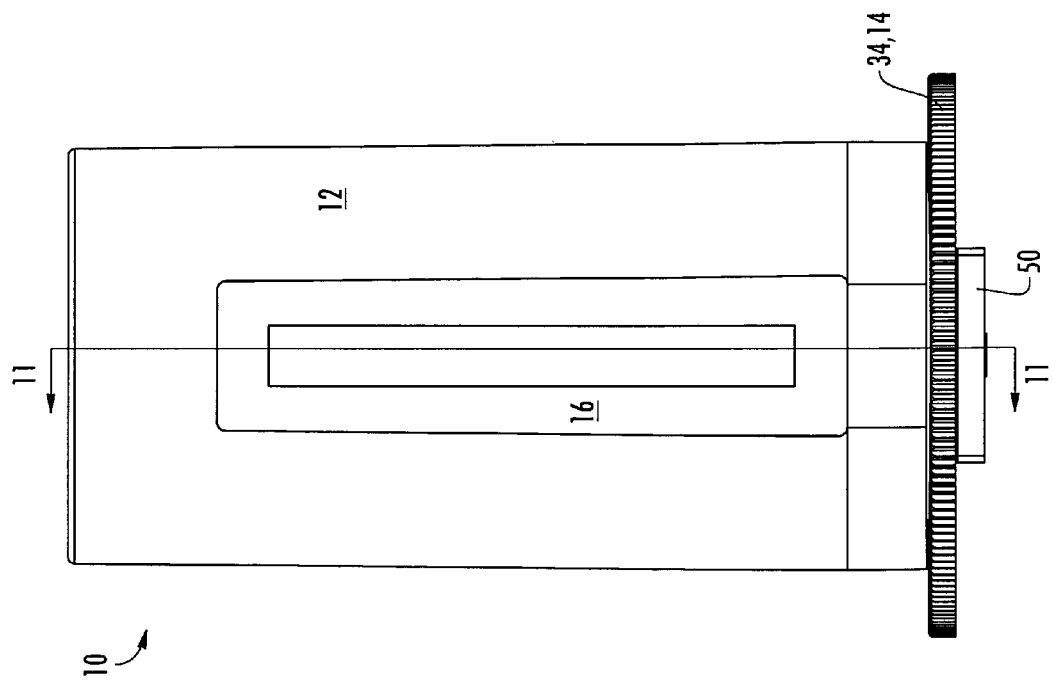
FIG. 4 is a top view of the test strip dispenser of FIG. 1.
Figure 5:
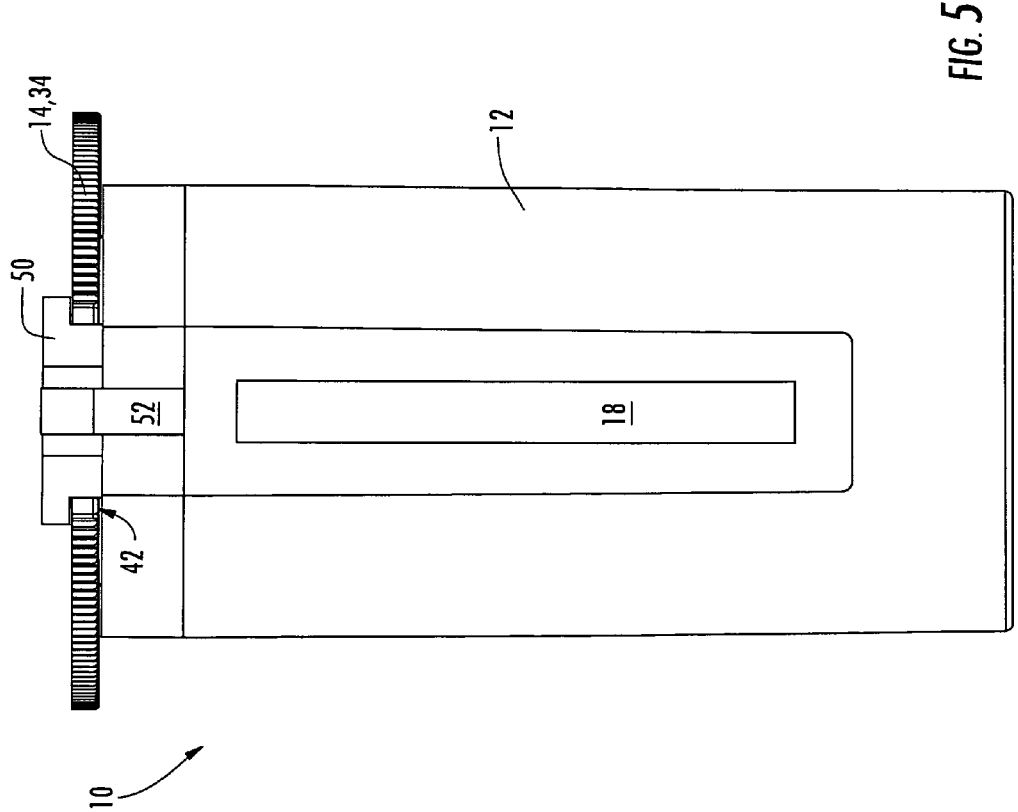
FIG. 5 is a bottom view of the test strip dispenser of FIG. 1.
Figure 6:
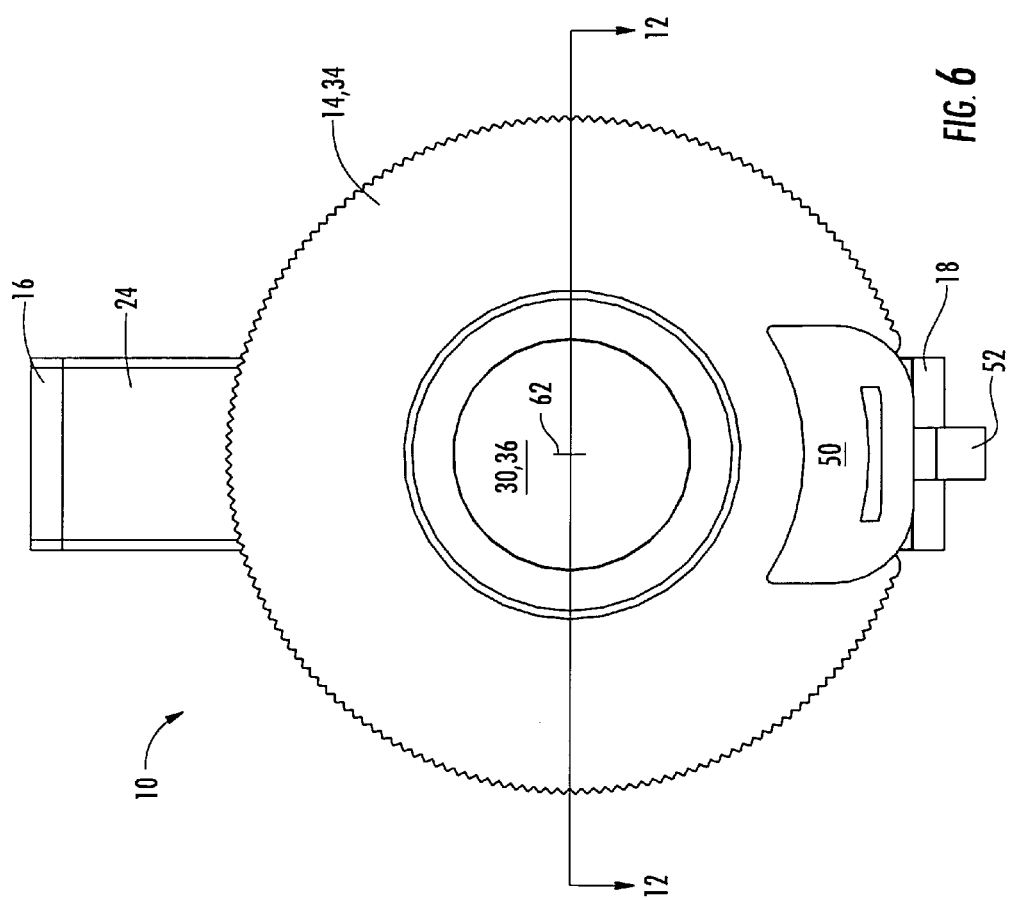
FIG. 6 is a front view of the test strip dispenser of FIG. 1.

Repeat use of reference characters in the present specification and drawings is intended to represent the same or analogous features or elements of the invention.

DETAILED DESCRIPTION OF REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

The present invention provides for a test strip dispenser 10 that allows one to dispense a test strip 22 that can be used to test any variety of substances. For example, the dispensed test strip 22 may be used to test a user's glucose level. The test strip dispenser 10 holds a plurality of test strips 20 and protects same from environmental contamination. The test strip dispenser 10 includes a cylindrical body 14 that defines a depression 40 that receives a test strip 22. The cylindrical body 14 rotates relative to a housing 12 that encapsulates the test strip 22 as it is rotated. The cylindrical body 14 defines a dispensing opening 28 through a portion of the cylindrical wall of the cylindrical body 14 and the test strip 22 falls from the depression 40 and through the dispensing opening 28 when the depression 40 moves into alignment with the dispensing opening 28. The test strip 22 is dispensed through a dispensing portion 27 of the housing 12 and the user will receive the dispensed test strip 22 without having to reach into the test strip dispenser 10 or drop any test strips 22 onto the floor during dispensing.

Figure 11:
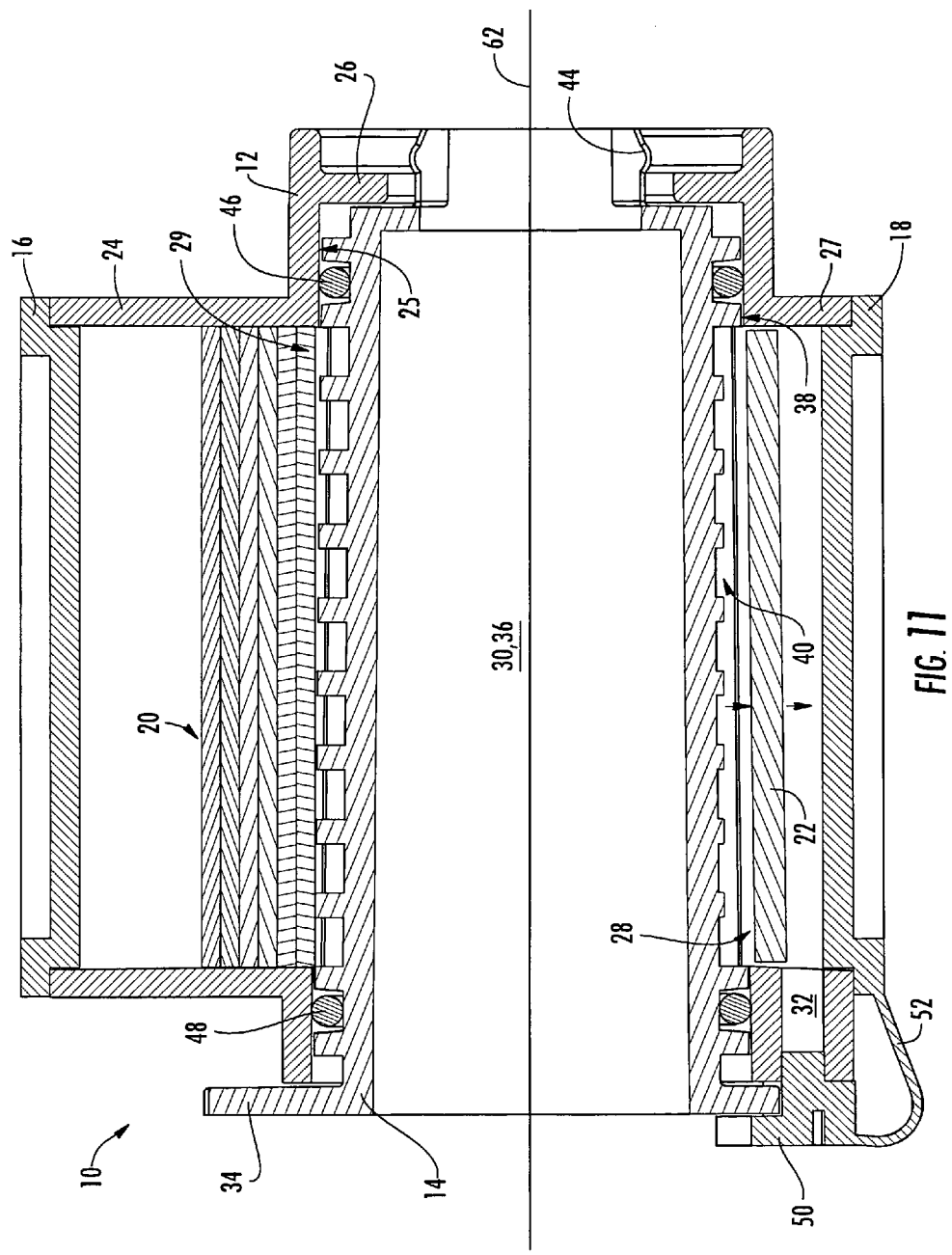
FIG. 11 is a cross-sectional view taken along line 11-11 of FIG. 4.

An exemplary embodiment of the test strip dispenser 10 is shown with reference to FIGS. 1-6. The test strip dispenser 10 includes a housing 12 that has a cylindrical wall portion with a central opening 30 that extends through the central axis of the cylindrical wall portion of the housing 12. Although both ends of the cylindrical wall portion of the housing 12 are open so that the central opening 30 is likewise open on both ends, other embodiments are possible in which one or both of the ends of the cylindrical wall portion are closed so that the central opening 30 is not a through opening. The housing 12 includes a magazine portion 24 that extends from the cylindrical wall portion of the housing 12 in a radial direction away from the cylindrical wall portion. The magazine portion 24 can be a generally rectangular shaped member and hollow with openings on both its upper and lower ends. With reference now to FIG. 11, the interior of the magazine portion 24 is shown in which a plurality of test strips 20 are disposed within the interior of the magazine portion 24. The test strips 20 can be rectangular in shape and can be stacked in single file on top of one another. Although six of the test strips 20 are shown as being located within the magazine portion 24, it is to be understood that any number of test strips 20 can be stored therein. As each one of the test strips 20 is dispensed, the height of the magazine of test strips 20 is reduced thus resulting in a space between the magazine of test strips 20 and the upper opening of the magazine portion 24.

The top of the magazine portion 24 is sealed by a top cap 16 that functions to prevent sunlight, water, and other contaminants from entering into the magazine portion 24 to potentially contaminate the test strips 20 held therein. The top cap 16 can be a plastic component that is removably attached to the top of the magazine portion 24 to close the upper opening of the top of the magazine portion 24. In one exemplary embodiment, the top cap 16 is made of a hard rubber material and is removably attached to the magazine portion 24 through a friction fit arrangement in which a central portion of the top cap 16 is frictionally fit within the upper opening of the top cap 16. The user may pull the top cap 16 off of the magazine portion 24 to open the magazine portion 24 so as to reveal the upper opening of the magazine portion 24 as can be seen with reference now to FIG. 8. The user may then place a new magazine of tests strips 20 into the magazine portion 24 through its upper opening and can then replace the top cap 16 onto the magazine portion 24 in order to refill the test strip dispenser 10. However, it is to be understood that other arrangements are possible in which the top cap 16 is not capable of being removed from the magazine portion 24. Here, the test strips 20 will be dispensed until they are completely depleted. The test strip dispenser 10 will be disposed of and the user can utilize a new test strip dispenser 10.

Figure 7:
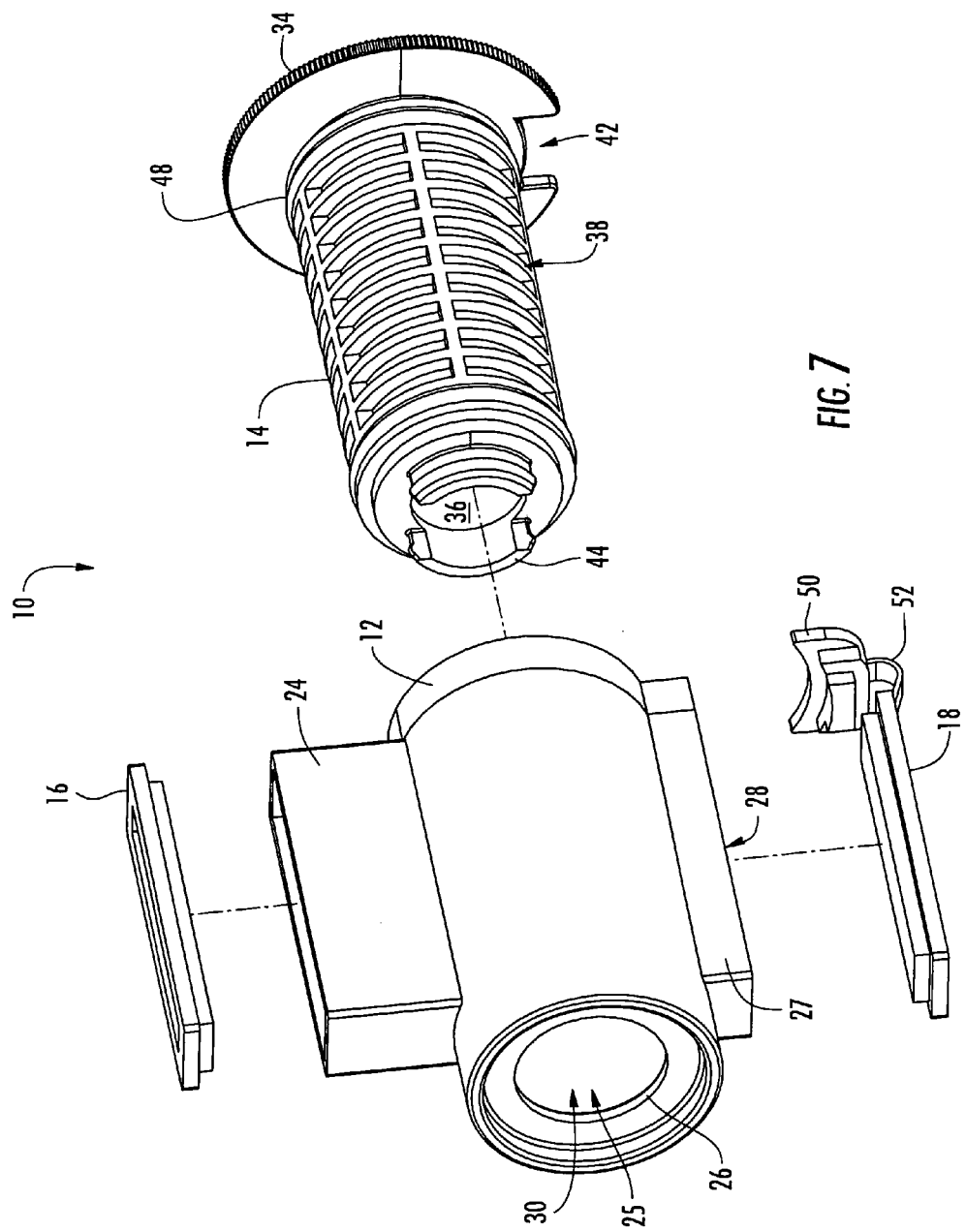
FIG. 7 is an exploded assembly view of the test strip dispenser of FIG. 1 from a generally rearward angle of the dispenser.
Figure 12:
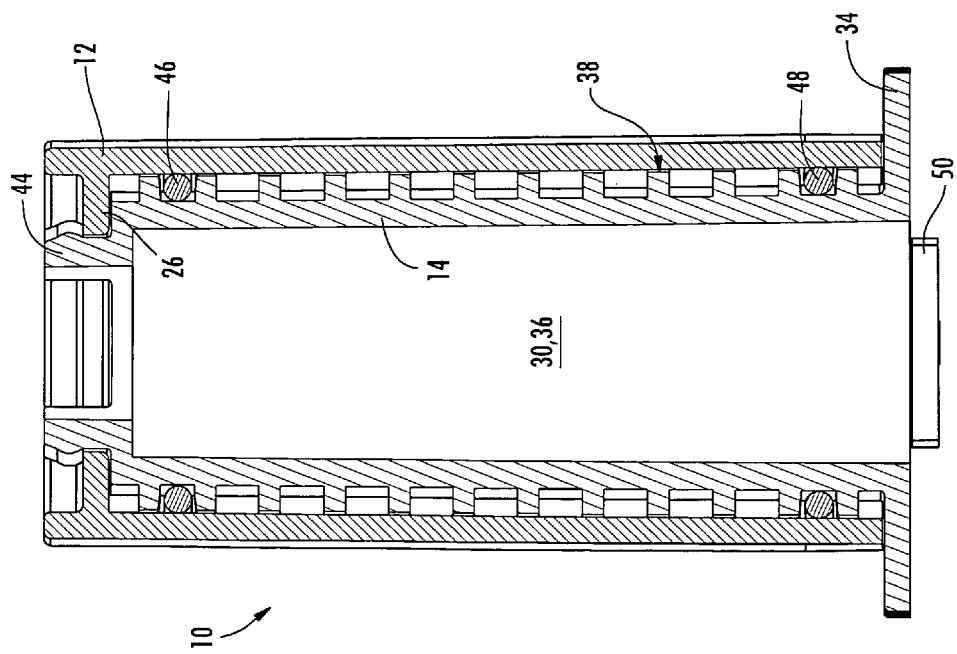
FIG. 12 is a cross-sectional view taken along line 12-12 of FIG. 6.

With reference now to FIG. 7, the housing 12 has a flange 26 that extends in the radial direction inward from the inner wall of the cylindrical wall portion of the housing 12. The flange 26 can extend completely 360° about the longitudinal axis of the cylindrical wall portion of the housing 12. In other arrangements, the flange 26 can extend less than 360° or may be discontinuous at one or more locations. The cylindrical body 14 of the test strip dispenser 10 is received into the central opening 30 of the housing 12. An engagement member 44 is located on one end of the cylindrical body 14 and includes two separate members that extend in the longitudinal direction of the cylindrical body 14. Each one of the members of the engagement member 44 includes a projection that extends in the outward radial projection. The engagement member 44 functions to attach the cylindrical body 14 to the housing 12 so that these two components are attached to one another. With reference to FIGS. 11 and 12, insertion of the cylindrical body 14 into the central opening 30 causes the engagement member 44 to engage the flange 26. Continued pressure may force the engagement member 44 to be deflected inwardly in the radial direction so that the projections of the engagement member 44 can be moved longitudinally past the flange 26. Once the projections are moved past flange 26, the engagement member 44 springs back into its original position and thus into the position illustrated in FIGS. 11 and 12 in which the projections of the engagement member 44 engage the flange 26 and function to retain the cylindrical body 14 to the housing 12. The flange 26 is disposed between the projections of the engagement member 44 on one side and a longitudinally disposed face of the cylindrical body 14 on the other to effect this retention.

The cylindrical body 14 is capable of rotating 360° with respect to the housing 12. The flange 26 is retained by the engagement member 44 to prevent longitudinal movement between cylindrical body 14 and the housing 12 but allows rotational movement between these components. An outer surface 38 of the cylindrical body 14 may engage the inner surface of the cylindrical wall portion of the housing 12. This engagement may be such that it functions to allow radial movement between the housing 12 and the cylindrical body 14 but include enough frictional or tolerance resistance so as to at least partially restrain longitudinal movement between the housing 12 and the cylindrical body 14. However, it is to be understood that the engagement between the engagement member 44 and the flange 26 may be such that this engagement is sufficient to provide the desired longitudinal restraint and desired degree or ease of radial movement between the housing 12 and the cylindrical body 14. Grooves and projections received within grooves or other mechanisms can be employed to place the housing 12 into rotating engagement with the cylindrical body 14.

A pair of O-rings 46 and 48 may be included with the cylindrical body 14 and can engage the cylindrical body 14 and the inner wall of the cylindrical wall portion of the housing 12. The O-rings 46 and 48 may function to prevent water or other contaminants from passing into the interior portions of the test strip dispenser 10 so as to contaminate the test strips 20. The O-rings 46 and 48 may be positioned on opposite sides of the interior of the magazine portion 24 so that moisture or other contaminants are prevented from passing between the housing 12 and the cylindrical body 14 and into the interior of the magazine portion 24. Likewise, the O-rings 46 and 48 may be located on opposite sides of a dispensing portion 27 of the housing 12 so that again moisture or other contaminants are prevented from moving between the housing 12 and cylindrical body 14 and into the interior of the dispensing portion 27 to contaminate the test strips 20 that may be in or pass through the interior of the dispensing portion 27.

Figure 8:
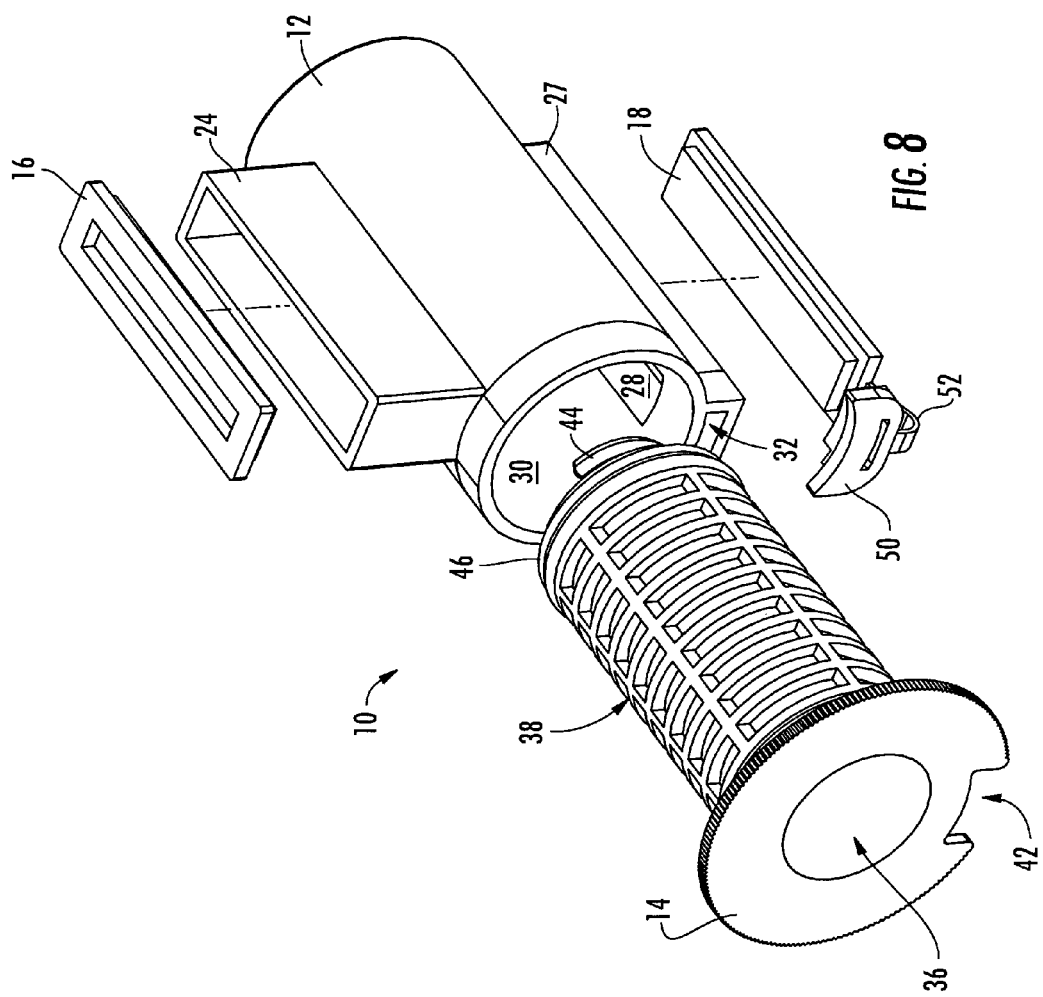
FIG. 8 is an exploded assembly view of the test strip dispenser of FIG. 1 from a generally frontward angle of the dispenser.
Figure 9:
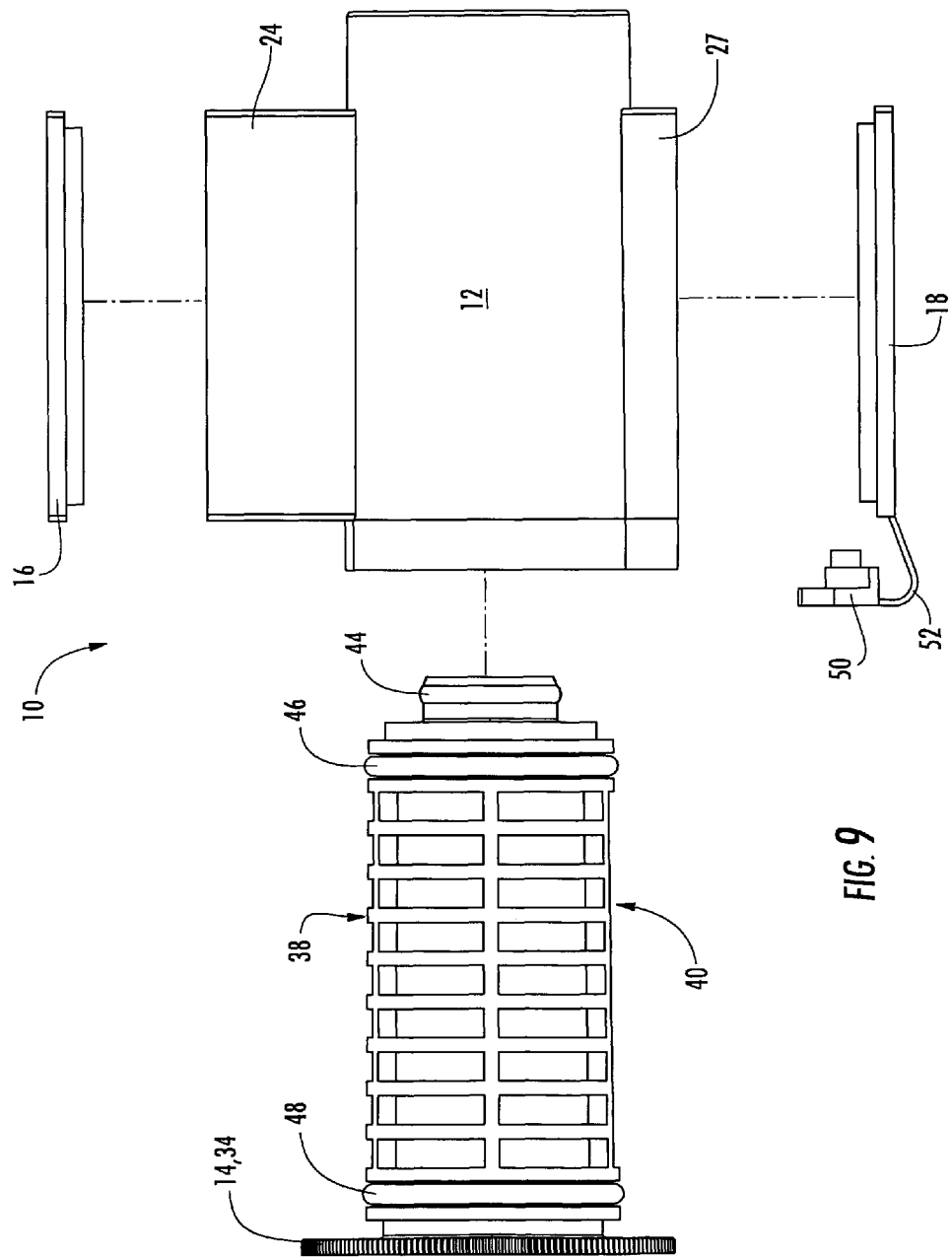
FIG. 9 is an exploded assembly view of the test strip dispenser of FIG. 1 from a generally side facing angle of the dispenser.

With reference now to FIGS. 8 and 11, the cylindrical body 14 includes a dial portion 34 that is located at one end. The dial portion 34 has a series of small grooves located on a radially facing surface that are capable of being grasped or otherwise manipulated by the user. The dial portion 34 is integrally formed or otherwise attached to the interior portion of the cylindrical body 14 that includes the outer surface 38 so that rotation of the dial portion 34 is translated to the outer surface 38 and other portions of the cylindrical body 14. As such, a user may grasp the test strip dispenser 10 and then turn the dial portion 34 to effect relative rotation between the cylindrical body 14 and the housing 12. The cylindrical body 14 may have a central opening 36 that extends completely through the cylindrical body 14 so as to be a through opening. The central opening 36 is coaxial with the central opening 30 and may be provided in order to reduce the weight and cost of the test strip dispenser 10. However, the central opening 36 may not be present in other embodiments or if present may not be arranged so as to extend completely through the cylindrical body 14 in other embodiments.

The dial portion 34 defines a notch 42 that extends in a radial direction of the dial portion 34. The notch 42 can extend along an arc length of 40° about the longitudinal axis of the dial portion 34. In other arrangements, the notch 42 may extend along an arc length that is from 40°-45°, from 30°-50°, from 20°-60°, or up to 75° about the longitudinal axis of the dial portion 34. The housing 12 may include a dispensing portion 27 that extends radially from the cylindrical wall portion of the housing 12. The dispensing portion 27 may define a locking member opening 32. In other exemplary embodiments, the locking member opening 32 may be defined by a different portion of the housing 12 and need not be defined by the dispensing portion 27.

The user may rotate the dial portion 34 until the notch 42 is aligned with the locking member opening 32. In this regard, the notch 42 may be located at the same radial position as the locking member opening 32 with respect to the coaxial longitudinal axes of the housing 12 and the cylindrical body 14. The user may insert a locking member 50 into the notch 42 and the locking member opening 32. The locking member 50 has a portion that is received within the locking member opening 32 and this receipt may be a frictional fit so that some degree of force is needed to insert this portion of the locking member 50 into the locking member opening 32. In other arrangements, no degree of force is needed to insert a portion of the locking member 50 into the locking member opening 32. The shape of the locking member opening 32 may be complimentary to the cross-sectional shape of the portion of the locking member 50 that is inserted into the locking member opening 32 so that they are the same. A portion of the locking member 50 will be located within the notch 42. This portion of the locking member 50 may be sized so that it spans the entire arc length of the notch 42 or may be sized so that it is less than the arc length of the notch 42. As such, the portion within the notch 42 may contact the dial portion 34 or may not contact the dial portion 34 in accordance with different exemplary embodiments. A portion of the locking member 50 may engage the front, longitudinally disposed face of the dial portion 34 in certain exemplary embodiments.

When inserted, the locking member 50 functions to lock the position of the cylindrical body 14 with respect to the housing 12 so that cylindrical body 14 does not rotate relative to the housing 12. The position of the locking member 50 is such that it is rigidly held within the locking mechanism opening 32 so that turning of the dial portion 34 will cause the edges of the dial portion 34 defining the notch 42 to contact the locking member 50 thus preventing the notch 42 from being moved past the locking member 50. The locking member 50 may be inserted when the test strip dispenser 10 is being stored or transported and is not being used to dispense test strips 20. When the dispensing of a test strip 20 is desired, the user may remove the locking member 50 from the locking mechanism opening 32 and out of the notch 42 to allow the cylindrical body 14 to rotate relative to the housing 12. The locking member 50 may be grasped for removal via its front portion that engages or is located adjacent to the front face of the dial portion 34.

Figure 13:
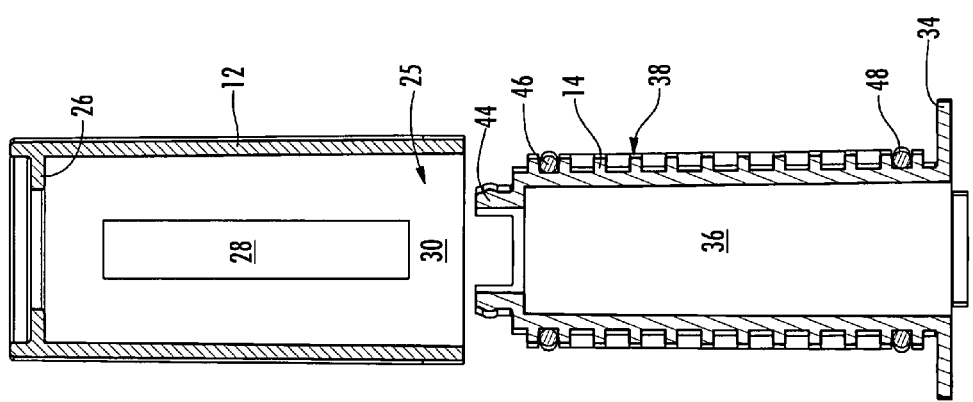
FIG. 13 is a cross-sectional view of the housing and the cylindrical body of the test strip dispenser of FIG. 1.
Figure 14:
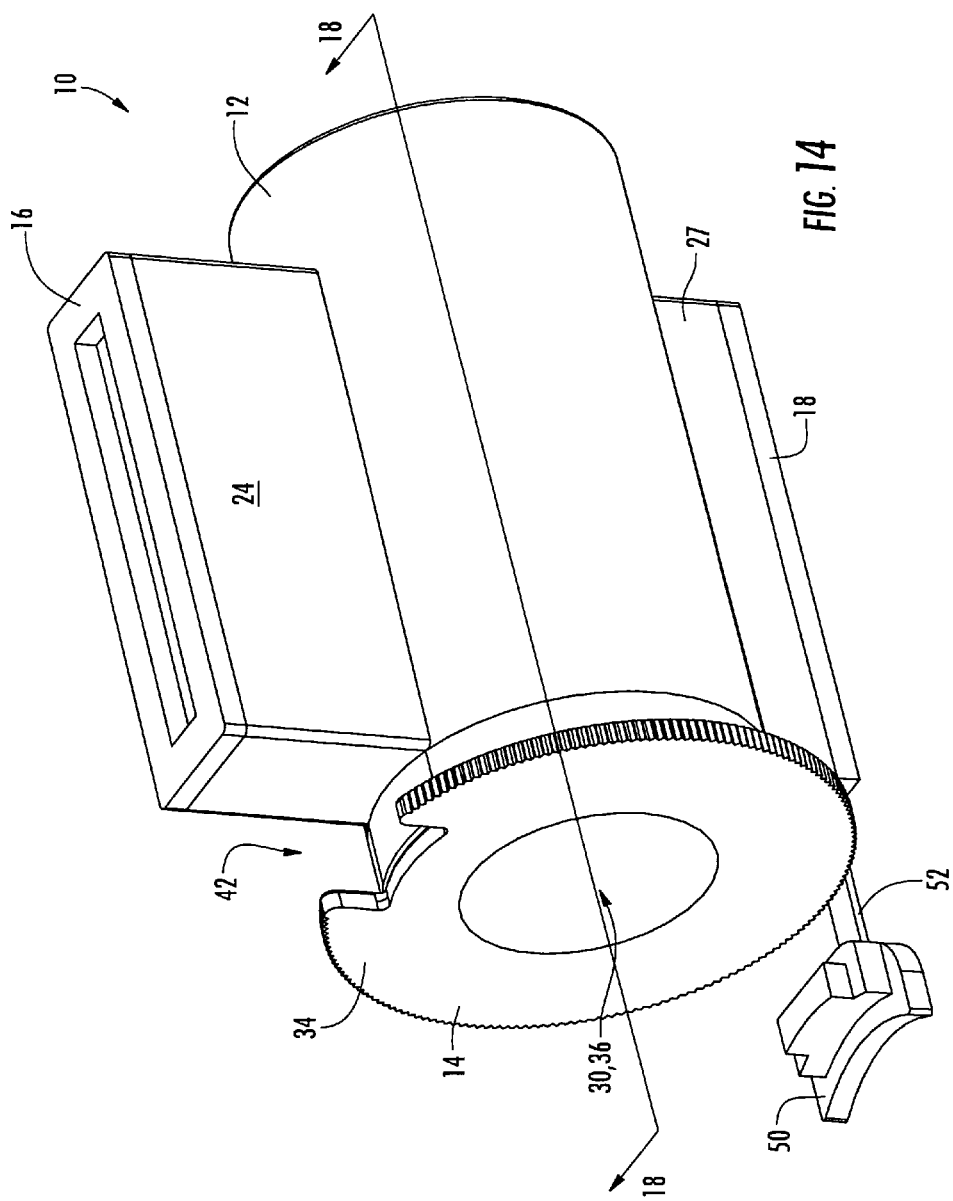
FIG. 14 is a perspective view of the test strip dispenser of FIG. 1 in a dispensing position.
Figure 15:
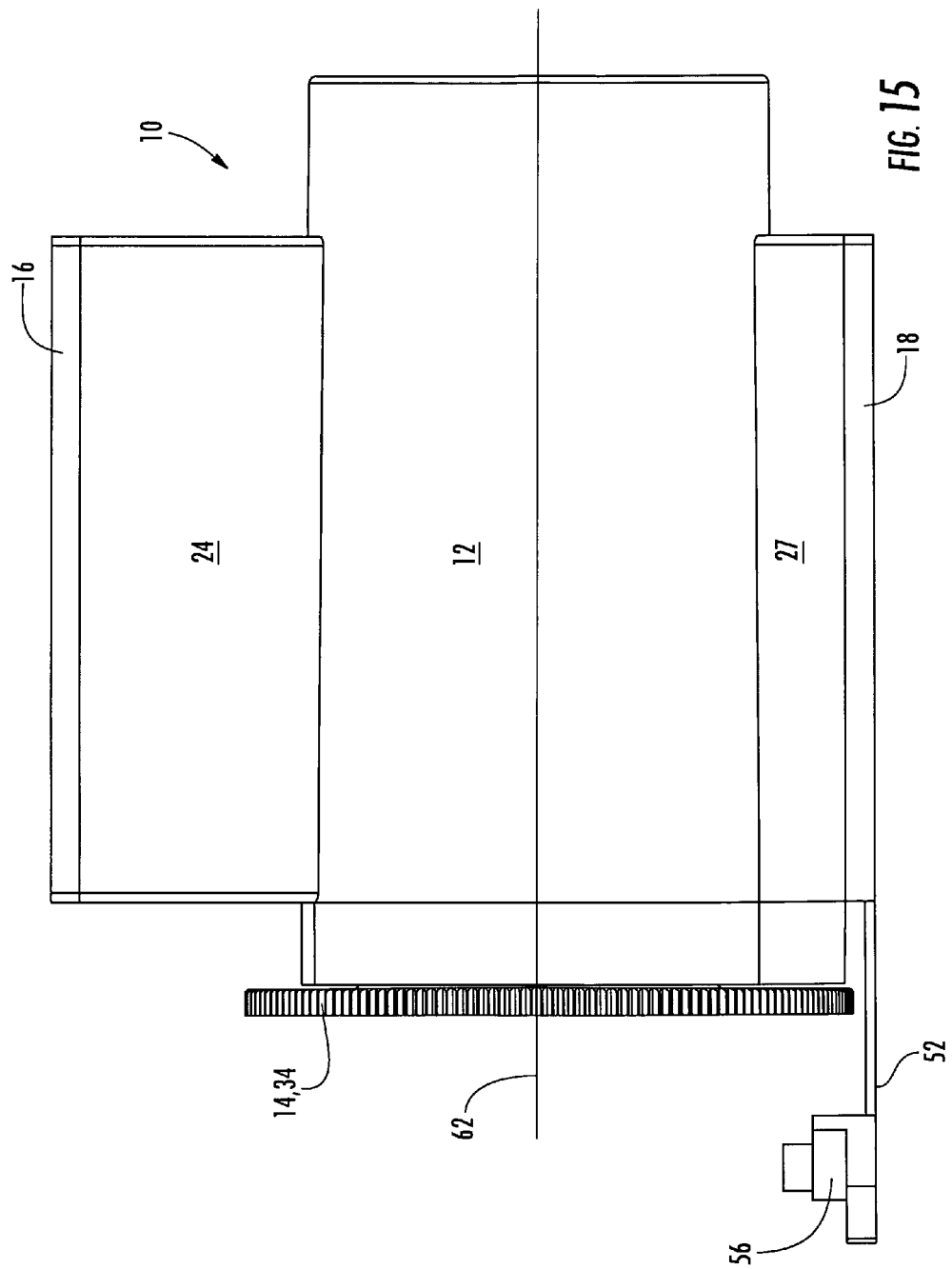
FIG. 15 is a side view of the test strip dispenser of FIG. 14.
Figure 16:
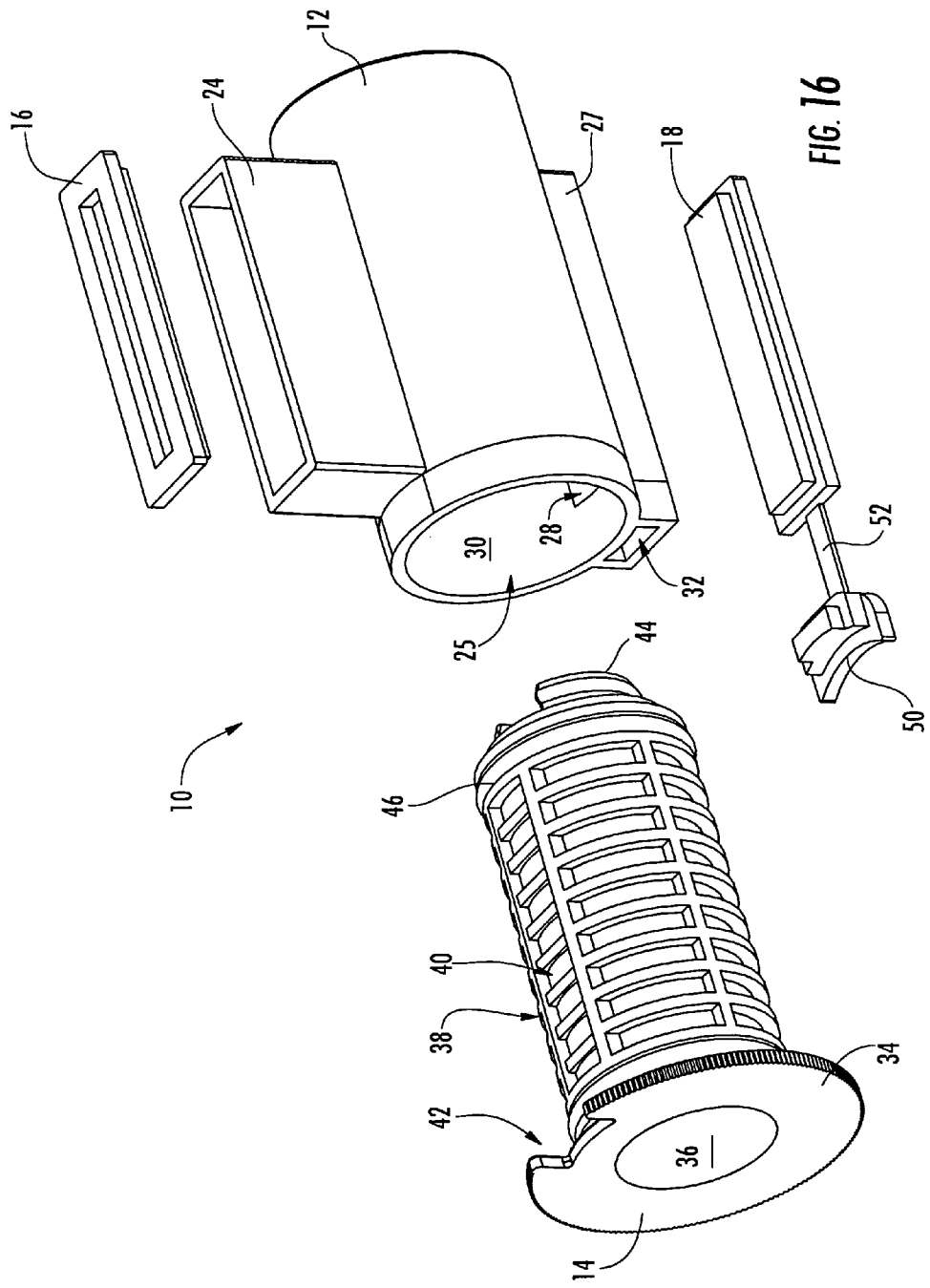
FIG. 16 is an exploded assembly view of the test strip dispenser of FIG. 14 from a generally forward angle of the dispenser.

The housing 12 may also include a dispensing portion 27 through which test strips 20 are dispensed. With reference to FIG. 13, a dispensing opening 28 is defined through the cylindrical wall portion of the housing 12 and is shaped so as to accommodate the size and shape of a test strip 20 that is to be dispensed. The dispensing portion 27 is shown in greater detail with reference to FIG. 11 in which the dispensing opening 28 extends through the cylindrical wall portion of the housing 12 and also through the dispensing portion 27. The dispensing portion 27 is sized and shaped so as to allow the test strip 20 to be moved therethrough. The dispensing portion 27 extends radially outward from the cylindrical wall portion of the housing 12 and can be located 180° about the longitudinal axis of the housing 12 from the magazine portion 24 so that it is on the other side of the housing 12 as the magazine portion 24. A test strip 22 may fall through the dispensing opening 28 in the dispensing portion 27 via gravity so as to exit the dispensing opening 28 and be dispensed to a user upon receipt just below the dispensing portion 27.

A bottom cap 18 may be positioned onto the dispensing portion 27 and into the dispensing opening 28 so as to close the dispensing opening 28. The bottom cap 18 may be attached to the dispensing portion 27 when the test strip dispenser 10 is being stored or transported or otherwise is not being used to dispense test strips 22. The bottom cap 18 can be frictionally fit onto the dispensing portion 27 so that a portion of the bottom cap 18 is sized and shaped in a manner similar to that of the dispensing opening 28 through the end of the bottom cap 18. The user can push the bottom cap 18 into the dispensing opening 28 so that the bottom cap 18 is retained thereon. When the user desires the test strip 22 be dispensed, he or she can pull the bottom cap 18 off of the dispensing portion 27 to afford access to the dispensing opening 28 so that the test strip 22 can be dispensed therefrom. Although shown and described as being frictionally fit, it is to be understood that the bottom cap 18 may be removably attached to the dispensing portion 27 in a variety of ways in accordance with different exemplary embodiments. The bottom cap 18 functions to prevent moisture and other contaminants from entering the internal portions of the test strip dispenser 10 to cause the test strips 22 to become contaminated. In the disclosed embodiment, a tether 52 attaches the locking member 50 to the bottom cap 18. In use, the user may remove the bottom cap 18 from the dispensing portion 27 and then remove the locking member 50 from the locking mechanism opening 32 to allow the test strip dispenser 10 to be actuated for dispensing of the test strip 22. The locking member 50 need not be tethered to the bottom cap 18 in other embodiments. This arrangement may assist the user in keeping the locking member 50 and the bottom cap 18 together to prevent either one of these parts from becoming lost.

With reference now to FIG. 8, it may be seen that the outer surface 38 of the cylindrical portion of the cylindrical body 14 defines a series of grate-like depressions that cause the outer surface 38 to be discontinuous. In other arrangements, the grate-like depressions are not present and the outer surface 38 can be smooth or otherwise free from depressions along at least a portion of its arc length. For example, the outer surface 38 may be free from depressions up to 315°, up to 300°, up to 270°, or from 0°-340° of the arc length about the longitudinal axis of the cylindrical body 14. The cylindrical body 14 is placed into engagement with the housing 12 so that the outer surface 38 directly faces a curved inner surface 25 of the housing 12. The outer surface 38 may engage the curved inner surface 25 or may not engage the curved inner surface 25. With reference back to FIG. 1, the cylindrical body 14 has an axis 62 that is coaxial with an axis of the curved inner surface 25.

Figure 10:
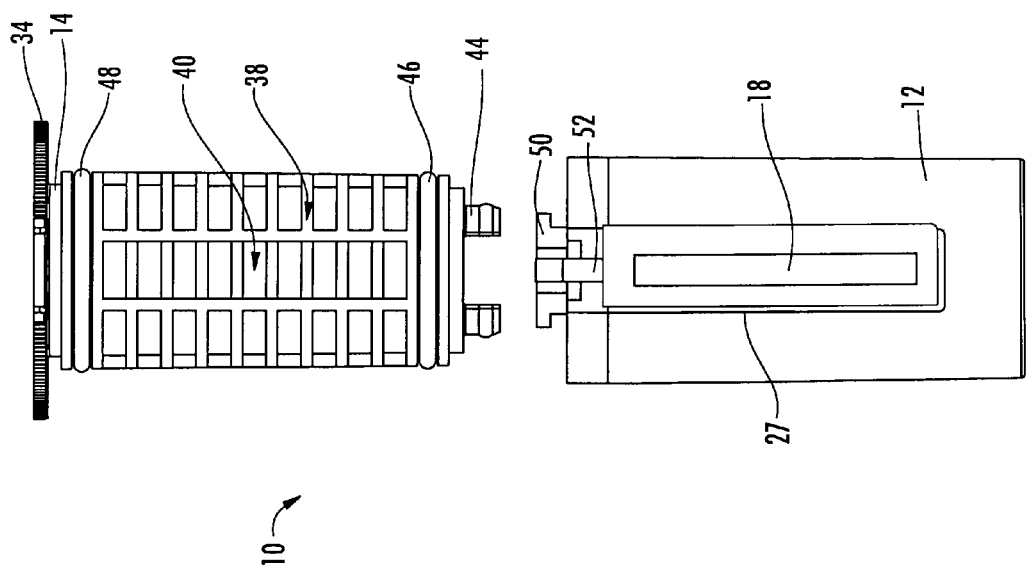
FIG. 10 is an exploded assembly view of the test strip dispenser of FIG. 1 from a generally bottom facing angle of the dispenser.

With reference now to FIG. 10, the outer surface 38 defines a depression 40 that is shaped and sized so as to accommodate receipt of a test strip 20. The depression 40 can have a rectangular shape upon looking down at the depression 40 so that a rectangular test strip 20 may be capable of being inserted into the depression 40. The user can rotate the dial portion 34 in order to rotate the outer surface 38 and hence the test strip 20 located in the depression 40 about the longitudinal axis of the cylindrical body 14. The depression 40 and carried test strip 20 can be rotated until the two of them are aligned with the dispensing opening 28 so that the test strip 20 can fall from the depression 40 via gravity and through the dispensing opening 28. The depression 40 may be located on the cylindrical body 14 so that the depression 40 and notch 42 are located next to one another and are at the same radial position about the longitudinal axis of the cylindrical body 14.

The depression 40 may be sized so that when the test strip 20 is within the depression 40, the entire test strip 20 is below portions of the outer surface 38 that are proximate to the test strip 20. In some instances, the portions of the outer surface 38 that are farthest from the axis 62 in the radial direction extend along the path of a circumference of a circle. The entire test strip 20 may be located below this circumference so that no portion of the test strip 20 within the depression extends radially beyond the circular circumferential path of the outer surface 38. Although shown as having a single depression 40, multiple depressions 40 may be included in the outer surface 38 in other embodiments and can be located at various angles from one another about the axis 62.

Figure 18:
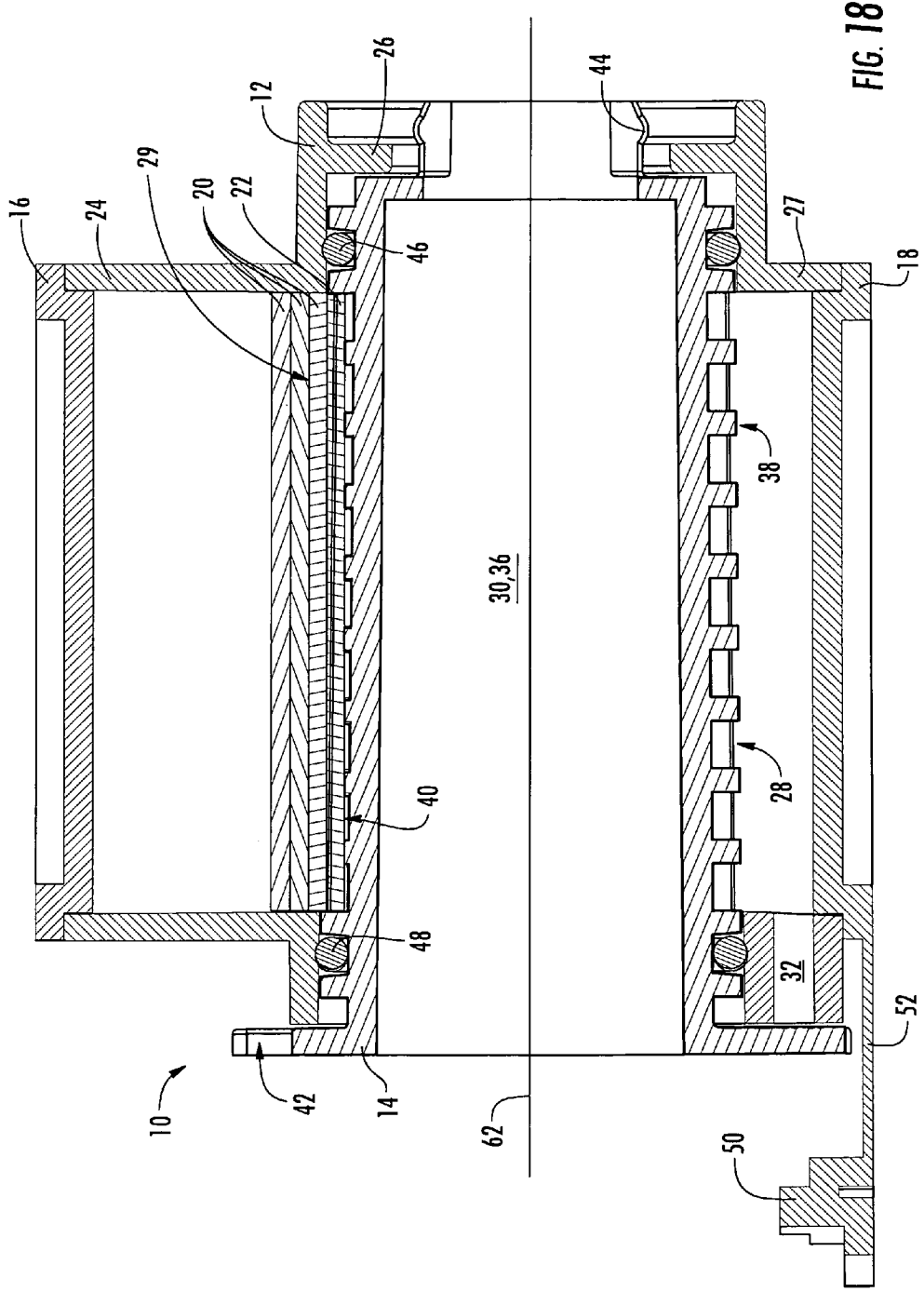
FIG. 18 is a cross-sectional view taken along line 18-18 of FIG. 14.
Figure 19:
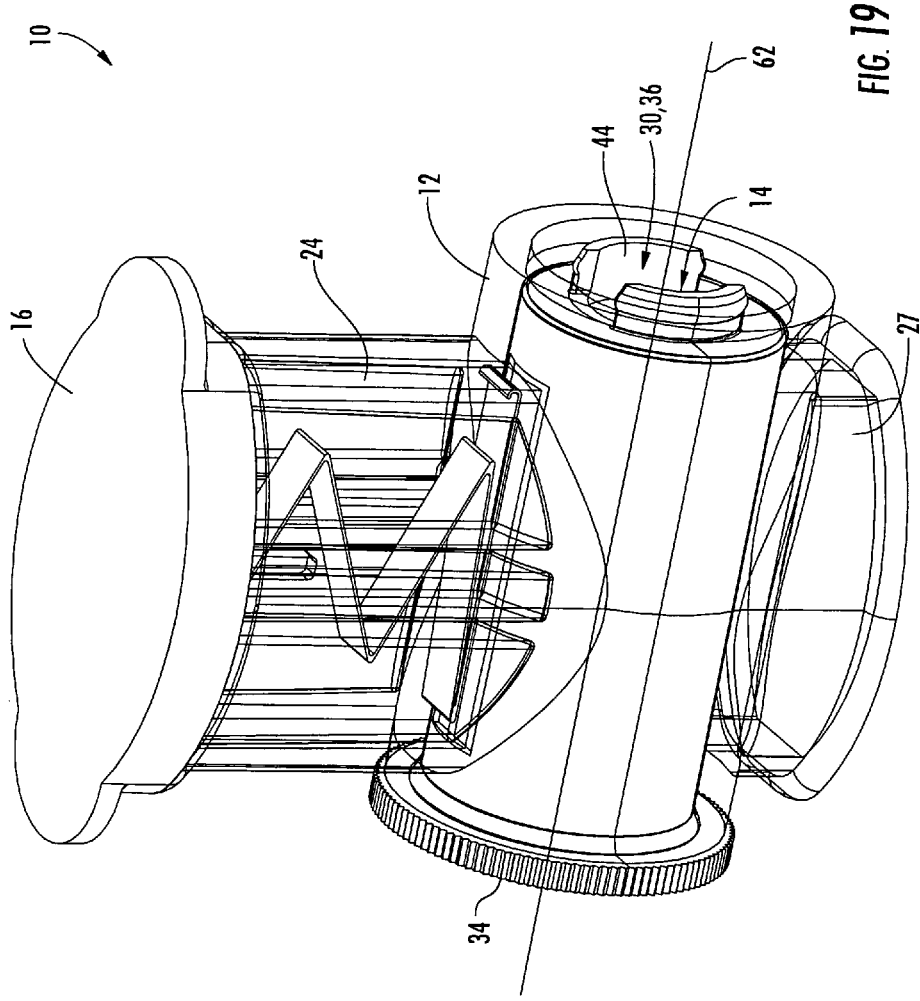
FIG. 19 is a perspective view of a test strip dispenser in accordance with another exemplary embodiment.

The functioning of the test strip dispenser 10 will now be described. Referring now to FIGS. 14-18, the user may first remove the locking member 50 from the locking mechanism opening 32 and the notch 42 to allow the dial portion 34 to be turned. The removed locking member 50 is illustrated and is attached to the bottom cap 18 via the tether 52. The user can rotate the dial portion 34 until the notch 42 is located at the top of its rotational travel path. This positioning will cause the depression 40 of the cylindrical body 14 to likewise rotate and be disposed at the very top of the cylindrical body 14. With reference in particular to FIG. 18, the depression 40 is sized so as to accommodate a single test strip 22 of the plurality of test strips 20. The test strip 20 on top of and contacting the single test strip 22 will be prevented from being disposed within the depression 40 because it will be located above the outer surface 38 and will be within the magazine portion 24. The test strip 22 may move through a magazine opening 29 and past the curved inner surface 25 and into the depression 40 via gravity or by way of other force, or by way of a combination of gravity and other force. The cylindrical body 14 and housing 12 may each be constructed with a tolerance that allows a single test strip 22 to be disposed within the depression 40 while the remaining test strips 20 are not disposed within the depression 40 and do not jamb the cylindrical body 14 upon subsequent rotation.

The user may rotate the dial portion 34 and cause the cylindrical body 14 to rotate, this will cause the depression 40 and test strip 22 within the depression to likewise rotate. The test strip 20 that was not received within the depression 40 will remain in the magazine portion 24 and will rest onto the rotating outer surface 38 of the cylindrical body 14. The user can rotate the dial portion 34 until the notch 42 is located at its lowermost point of travel. In this arrangement, the depression 40 and notch 42 will be positioned back into the location shown in FIG. 11. The depression 40 is moved into alignment with the dispensing opening 28. The test strip 22 will fall out of the depression 40 via gravity since no portion of the inner surface of the cylindrical wall portion of the housing 12 will at this point engage the test strip 22. The test strip 22 will fall through the dispensing opening 28 and out of the dispensing portion 27. Although FIG. 11 shows the bottom cap 18 closing the dispensing portion 27, it is to be understood that during use the user will remove the bottom cap 18 to allow the dispensing portion 27 to be open to expose the dispensing opening 28 to allow the test strip 22 to fall therethrough. Alternatively, the user may manipulate the test strip device 10 so that the test strip 22 falls onto the bottom cap 18 and then subsequently remove the bottom cap 18 to retrieve the dispensed test strip 22. Once the dispensing of the test strip 22 is accomplished, the user can reinsert the locking member 50 into the notch 42 and the locking mechanism opening 32 to again restrain relative rotation between the cylindrical body 14 and the housing 12. The user may also reattach the bottom cap 18 to help prevent contamination of the interior of the test strip dispenser 10.

The test strip dispenser 10 can function to dispense a single test strip 22 at a time. The user may use a single hand to effectuate dispensing. Alternatively, the user may use both hands to manipulate the test strip dispenser 10 to cause the test strip 22 to be dispensed. The test strip dispenser 10 can be arranged so that no springs or mechanical linkages are needed in order to bias the test strips 20 or pull the test strips 20 for dispensing. The test strip 22 can be dispensed simply through rotation and gravity. The test strip 22 can be dispensed without the use of a spring or sliding member thus simplifying the design of the test strip dispenser 10 to realize cost savings and a more robust design. However, it is to be understood that other arrangements are possible in which a spring and/or mechanical linkage such as a sliding mechanism is used with the test strip dispenser 10. The rotation of the cylindrical body 14 with depression 40 functions to keep the test strips 20 in the magazine portion 24 isolated from the dispensing portion 27 so that if contamination were present in the dispensing portion 27, it would be impeded from traversing to the magazine portion 24 to contaminate the test strips 20 at this location. The various components of the test strip dispenser 10 can be made from any suitable materials. For example, the housing 12, cylindrical body 14, top cap 16 and bottom cap 18 may be made of plastic in accordance with certain exemplary embodiments.

An additional exemplary embodiment of the test strip dispenser 10 is illustrated in FIGS. 19-24. As shown with reference first to FIG. 19, the test strip dispenser 10 has a magazine portion 24 and a dispensing portion 27 of the housing 12 that are shaped and configured differently from those previously described. The end of the housing 12 is open so that the engagement members 44 of the cylindrical body 14 are visible. However, in other embodiments, the end of the housing 12 may be closed so that one cannot see the engagement members 44 or other portions of the cylindrical body 14. A top cap 16 is placed over the top of the magazine portion 24 in order to close the top of the magazine portion 24 as previously described. The top cap 16 can be engaged through the use of a frictional attachment and can have a pair of flanges on opposite sides that can be grasped and pulled by the user for disengagement. The top cap 16 can be moved down onto a flange of the magazine portion 24 of the housing 12.

Figure 20:
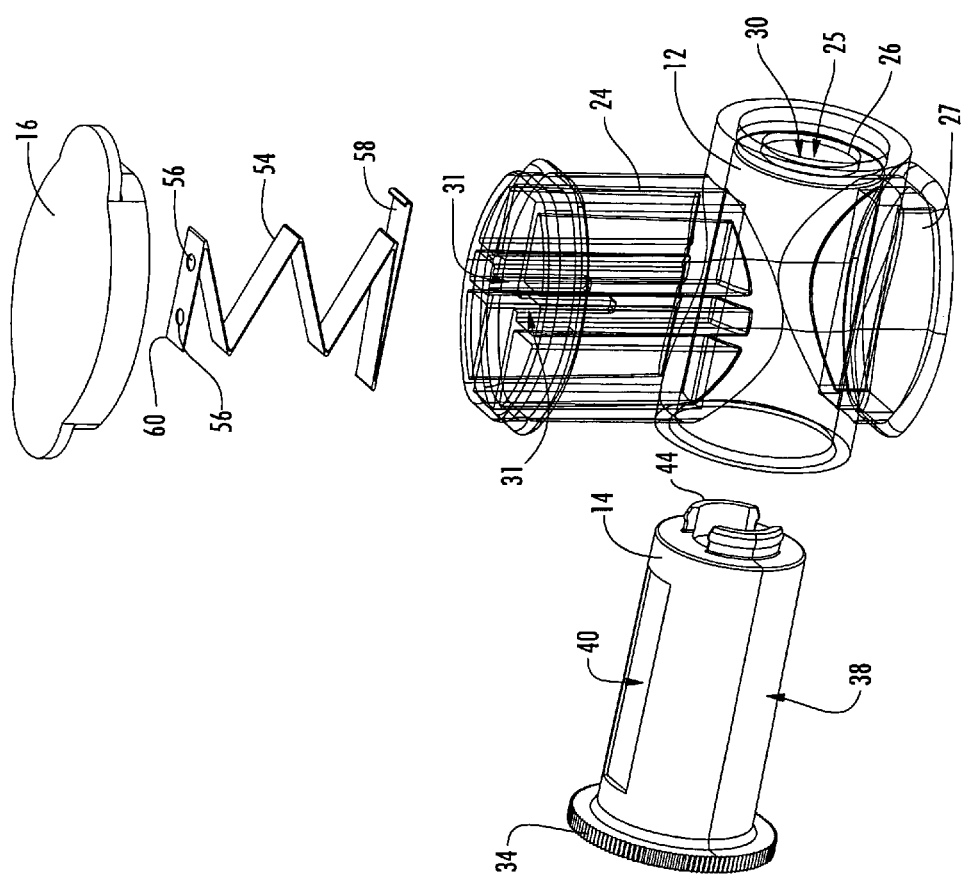
FIG. 20 is an exploded perspective assembly view of the test strip dispenser of FIG. 19.

FIG. 20 is an exploded perspective view of the test strip dispenser 10 in which a spring member 54 is shown. The spring member 54 is located within the magazine portion 24 of the housing 12 in order to urge the stack of test strips 20 towards the cylindrical body 14. As shown, the spring member 54 is biased outwards from itself so that if one were to compress the spring member 54 on its top and bottom ends, it will expand in the top and bottom directions if this compression were released. The spring member 54 has a number of arms that can bend relative to one another such that they will be in close proximity or actually touching one another when the spring member 54 is compressed, and will be farther from one another when the spring member 54 is in an extended state. The spring member 54, or at least the arms of the spring member 54, may be made of a resilient material that can be bent and then regains its shape once the force is removed or reduced such as spring steel.

Figure 22:
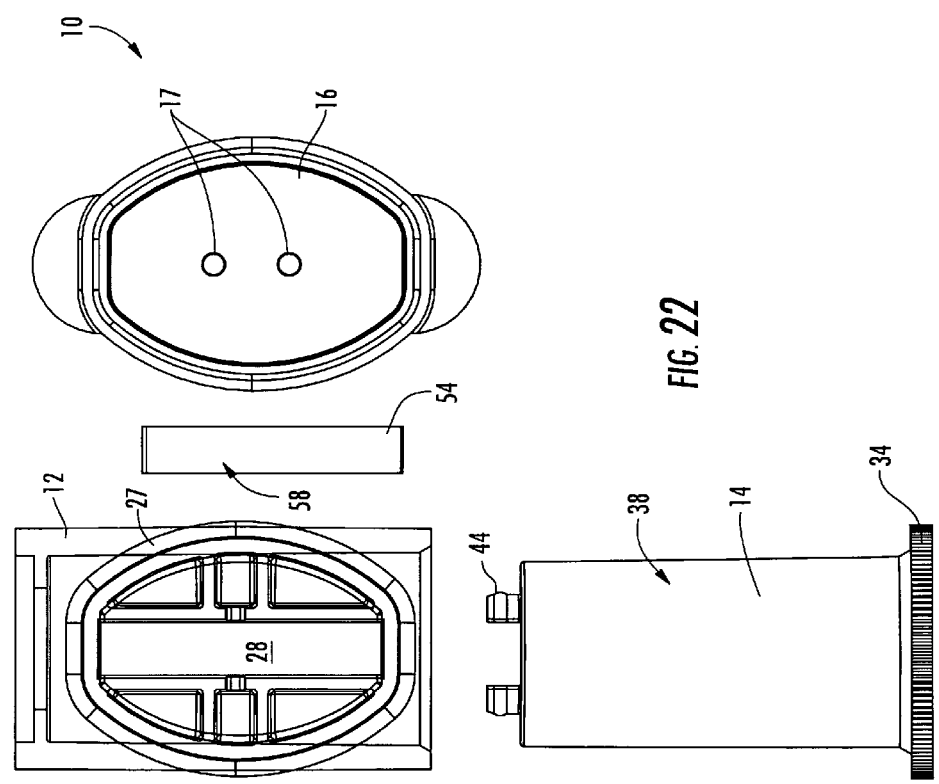
FIG. 22 is an exploded bottom assembly view of the test strip dispenser of FIG. 19.

The spring member 54 has a top plate 60 that engages a bottom of the top cap 16. The top plate 60 has a pair of apertures 56 that extend completely through the top plate 60. With reference now to FIG. 22, the top cap 16 has a pair of projections 17 that extend downward from the bottom surface of the top cap 16. The apertures 56 can be fit over the projections 17 such that a frictional attachment between the spring member 54 and the top cap 16 is realized. In other arrangements, the projections 17 and apertures 56 are not frictionally engaged such that the placement of the apertures 56 onto the projections 17 functions as a hold or guide and not as a direct attachment of the top cap 16 and the spring member 54. It is to be understood that the engagement of the top cap 16 and spring member 54 disclosed is only exemplary and that others are possible. For example, the top plate 60 may not have the apertures 56 and can simply rest against the bottom surface of the top cap 16 or the projections 17 of the top cap 16 if present.

Figure 21:
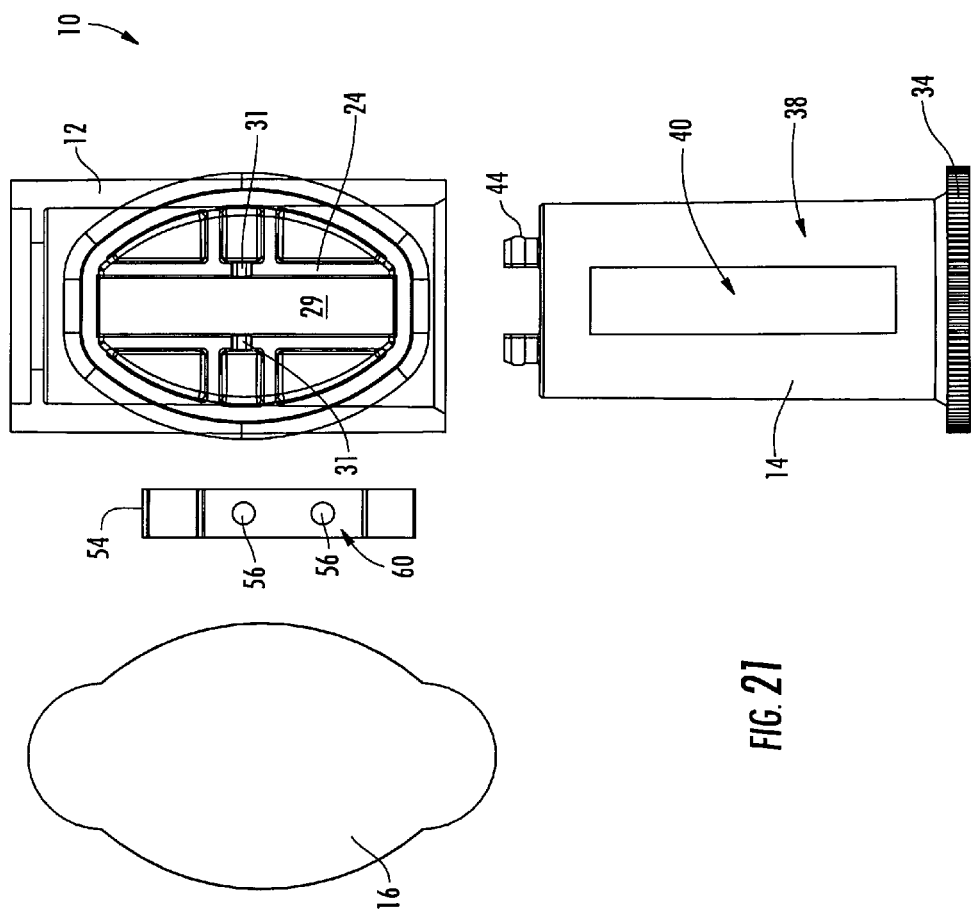
FIG. 21 is an exploded top assembly view of the test strip dispenser of FIG. 19.

The opposite end of the spring member 54 has a face plate 58 that may be seen with reference back to FIG. 20. The face plate 58 may be made out of the same material as the rest of the spring member 54, such as the arms, or may be made out of a different material. The spring member 54 is inserted into the magazine portion 24 such that the face plate 58 extends first into the magazine portion 24 followed by the arms and then the top plate 60. The magazine portion 24 defines a chamber that receives the magazine of test strips 20 and the spring member 54. With reference now to FIGS. 20 and 21, the magazine portion 24 has a number of interior walls that form a rectangular shaped chamber sized to hold the test strips 20. The interior chamber can be sized and shaped differently in other arrangements. The end walls of the chamber are closed along their lengths. However, the side walls of the chamber each have a magazine opening 31 that extends some portion of their lengths downwards from the top of the magazine portion 24. The magazine openings 31 may extend ⅓ of the height of the chamber, or may extend ½ of the height of the chamber. The magazine openings 31 may reduce pressure on the walls of the chamber to function to allow the test strips 20 to slide more easily within the chamber. In other exemplary embodiments, the magazine openings 31 are not present.

The dispensing portion 27 of the housing 12 has a generally oval shape that as shown in FIG. 22 may extend outwards beyond the perimeter of the other portions of the housing 12 when viewed from the bottom. The dispensing portion 27 has a lip at its bottom, terminal end. The housing defines a dispensing opening 28 large enough to accommodate the transfer of test strips 20 upon dispensing. The cylindrical body 14 in the disclosed embodiment has an outer surface 38 that lacks grooves and instead is generally smooth. A depression 40 is formed in the outer surface 38. A notch 42 of the dial portion 34 is not present, and the dial portion 34 extends 360° about its axis. An engagement member 44 functions to connect the cylindrical body 14 to the flange 26 so that the axes of the openings 30 and 36 are coaxial. A pair of O-rings 46 and 48 are not present.

Figure 23:
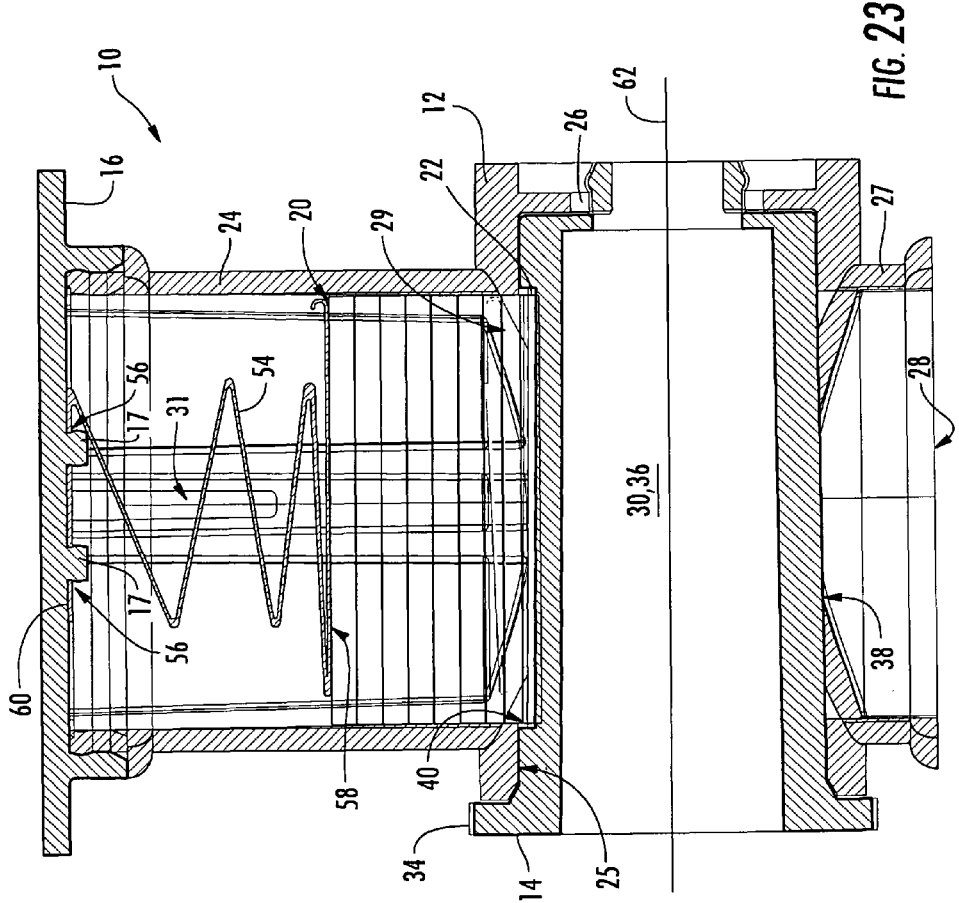
FIG. 23 is a cross-sectional view of the test strip dispenser of FIG. 19 in which a stack of test strips are present.

Reference is not made to FIG. 23. A stack of test strips 20 are located within the chamber of the dispensing portion 27. The test strips 20 are stacked on top of one another and the very bottom test strip 22 is disposed within the depression 40. The spring member 54 is located between the test strips 20 and the top cap 16. The face plate 58 engages the upper one of the test strips 20 and due to the biasing of the spring member 54, the spring member 54 urges the test strips 20 towards the cylindrical body 14. This arrangement may ensure that the test strips 20 do not move within the dispensing portion 27 such that the test strip 22 is located outside of the depression 40. The user may rotate the cylindrical body 14 in a manner previously described so that the test strip 22 within the cylindrical body 14 is rotated to and then out of the dispensing opening 28 and out of the dispensing portion 27 of the housing 12 for receipt by the user. The spring member 54 allows the test strip 22 to be loaded within the depression 40 regardless of the orientation of the test strip dispenser 10. However, once rotated to the dispensing opening 28, it may be the case that the housing 12 has to be positioned right side up, that is so that the magazine portion 24 is located above the dispensing portion 27, so that the test strip 22 may fall through the dispensing opening 28 via gravity and out of the dispensing portion 27 for retrieval by the user.

Figure 24:
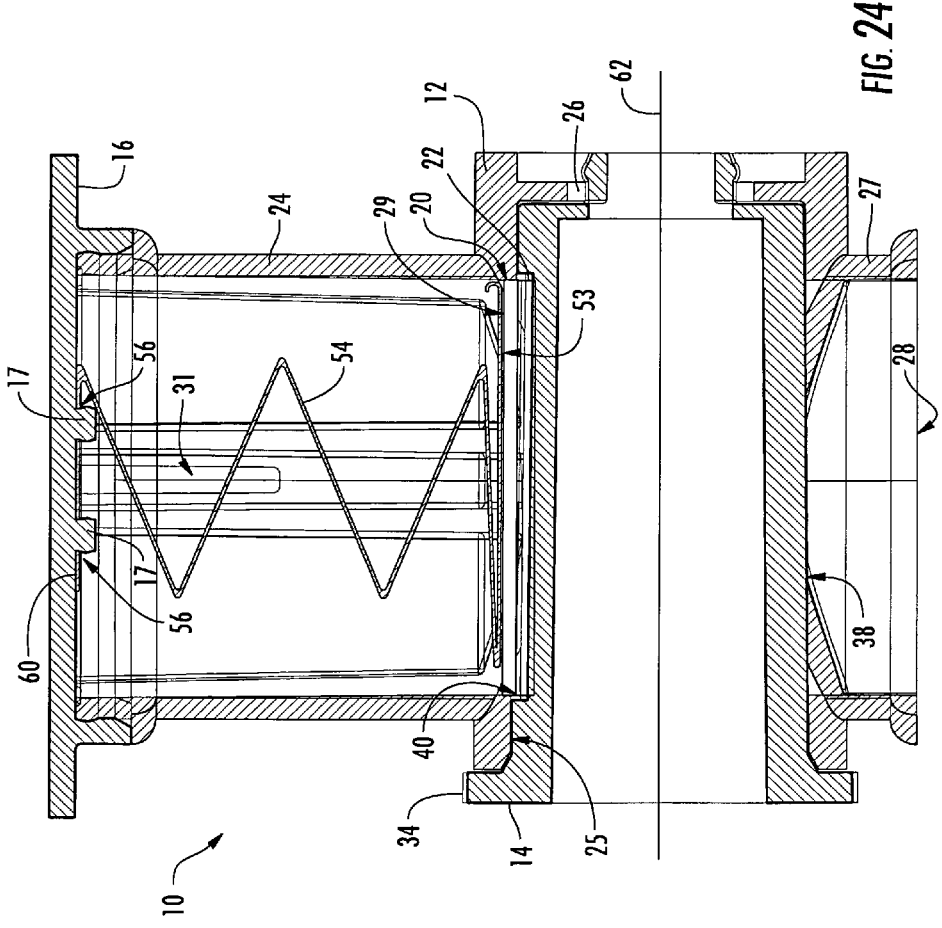
FIG. 24 is a cross-sectional view of the test strip dispenser of FIG. 19 in which a smaller stack of test strips than the stack in FIG. 23 are present.

Once the stack of test strips 20 becomes reduced, the spring member 54 will expand so that it becomes longer in the up/down direction. FIG. 24 is a view of the test strip dispenser 10 after the plurality of test strips 20 has been reduced from that illustrated in FIG. 23. As shown, the spring member 54 is expanded so that the face plate 58 is located farther from the top cap 16 than it was in FIG. 23. The face plate 58 still functions to contact the upper test strip 20 so that the lower test strip 22 is pushed into the depression 40. When the depression 40 is not located in alignment with the magazine portion 24 at the magazine portion 24, the spring member 54 functions to press the lower test strip 22 against the outer surface 38. Once the final test strip 20 is dispensed, the face plate 58 may be forced down into the depression 40 once the depression 40 is again aligned with and at the magazine portion 24. Rotation of the cylindrical body 14 will be prevented because of the spring member's 54 presence in both the depression 40 and the chamber of the magazine portion 24. This locking may indicate to the user that the magazine portion 24 is empty of test strips 20. In other arrangements, the face plate 58 will reach maximum extension at a location short of the depression 40 so that the face plate 58 will not enter the depression 40 or prevent relative rotation between the cylindrical body 14 and the housing 12.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A test strip dispenser comprising:
a housing that defines a magazine portion adapted for holding a plurality of test strips, the magazine portion in further communication with a dispensing opening which extends through a curved inner surface defined by the housing and through which the test strip moves from the magazine portion into the depression, wherein the magazine opening and the dispensing opening are positioned 180° from one another about an axis, the magazine further comprising a locking mechanism opening;
a cylindrical body that is rotatably attached to the housing, wherein the cylindrical body having a dial portion having a diameter greater than a diameter of the cylindrical body, and the cylindrical body is capable of rotating about an axis such that the cylindrical body rotates relative to the housing; and the dial portion further defining a notch;
a locking member that when located within both the notch and the locking mechanism opening effects a locking of the cylindrical body such that the cylindrical body is prevented from rotating about the axis relative to the housing, wherein the locking member is removable from the notch and the locking mechanism opening to effect unlocking of the cylindrical body such that the cylindrical body is capable of rotating about the axis relative to the housing; and
wherein when one of the plurality of test strip engages an outer surface of the cylindrical body and that is carried by the cylindrical body about the axis as the cylindrical body rotates about the axis, wherein alignment of the one of the plurality of test strips with the dispensing opening causes the test strip to fall off of and out of engagement with the outer surface of the cylindrical body and through the dispensing opening.

2. The test strip dispenser as set forth in claim 1, wherein the outer surface of the cylindrical body has a depression, and wherein the test strip when engaging the outer surface of the cylindrical body is located entirely within the depression, and wherein when the test strip falls off of and out of engagement with the outer surface of the cylindrical body the test strip falls out of the depression.

3. The test strip dispenser as set forth in claim 2, wherein the depression has a depth of such a size that when the test strip is located in the depression the entire test strip is located at or below the height of surrounding portions of four edge walls of the depressing.

4. The test strip dispenser as set forth in claim 1, wherein the test strip first engages the outer surface of the cylindrical body at a location that is located 180° about the axis from the location where the test strip disengages the cylindrical body and falls through the dispensing opening such that the test strip and the cylindrical body rotate 180° about the axis and do not rotate completely about the axis between the location where the test strip first engages the outer surface of the cylindrical body and the location where the test strip disengages the outer surface of the cylindrical body.

5. The test strip dispenser as set forth in claim 1, wherein the cylindrical body has an engagement member located on one end and a dial portion located on an opposite end, wherein the body has a flange, wherein the engagement member engages the flange to cause the cylindrical body to be in rotational engagement with the housing, wherein the dial portion has a diameter that is larger than the diameter of the outer surface of the cylindrical body, wherein the dial portion has a plurality of grooves thereon and wherein the dial portion is capable of being rotated by the user to cause the cylindrical body to be rotated relative to the housing.

6. The test strip dispenser as set forth in claim 1, wherein the housing has a magazine portion that has a chamber in which a stack of test strips are located, wherein once one of the test strips is carried by the cylindrical body and falls off of and out of engagement with the outer surface of the cylindrical body and through the dispensing opening another one of the test strips from the stack of test strips is available for subsequent carrying and disengagement from the outer surface of the cylindrical body and through the dispensing opening;
wherein the housing has a dispensing portion, wherein when the test strip falls through the dispensing opening the test strip subsequently falls through the dispensing portion and out of the test strip dispenser, wherein the test strip falls via gravity off of and out of engagement with the outer surface of the cylindrical body and through the dispensing opening and through the dispensing portion and out of the test strip dispenser.

7. The test strip dispenser as set forth in claim 1, further comprising a spring member that urges the test strip into engagement with the outer surface of the cylindrical body, wherein a certain amount of rotation of the cylindrical body about the axis causes the test strip to be moved to a location in which the spring member no longer urges the test strip into engagement with the outer surface of the cylindrical body.

8. The test strip dispenser as set forth in claim 1, wherein the housing has a magazine portion and a dispensing portion, wherein the magazine portion is located 180° about the axis from the dispensing portion, wherein the test strip is located in the magazine portion before engagement with the outer surface of the cylindrical body, wherein when the test strip falls through the dispensing opening the test strip subsequently falls into the dispensing portion;
further comprising a top cap that is located on the magazine portion and that is removable from the magazine portion; and
a bottom cap that is located on the dispensing portion and that is removable from the dispensing portion.

9. The test strip dispenser as set forth in claim 8, wherein the locking member is attached to the bottom cap by a tether.

10. A test strip dispenser, comprising:
a housing that has a magazine portion, wherein the housing has a curved inner surface and wherein a dispensing opening extends through the curved inner surface, the magazine further comprising a locking mechanism opening;
a cylindrical body that is rotatably attached to the housing, wherein the cylindrical body is capable of rotating about an axis, wherein the cylindrical body has an outer surface that defines a depression, wherein the outer surface of the cylindrical body directly faces the curved inner surface of the housing the cylindrical body having a dial portion having a diameter greater than a diameter of the cylindrical body, a locking member that when located within both the notch and the locking mechanism opening effects a locking of the cylindrical body such that the cylindrical body is prevented from rotating about the axis relative to the housing, wherein the locking member is removable from the notch and the locking mechanism opening to effect unlocking of the cylindrical body such that the cylindrical body is capable of rotating about the axis relative to the housing; and, a test strip stored in the magazine portion and that moves from the magazine portion into the depression, wherein the magazine opening extends through the curved inner surface through which a test strip moves from the magazine portion into the depression, wherein the magazine opening and the dispensing opening are positioned 180° from one another about the axis and wherein relative rotation of the cylindrical body with respect to the housing causes the test strip in the depression to be moved such that the test strip directly faces the curved inner surface of the housing until the test strip is aligned with the dispensing opening at such time the test strip falls out of the depression and through the dispensing opening.

11. The test strip dispenser as set forth in claim 10, wherein the cylindrical body is capable of rotating 360° about the axis, and wherein the curved inner surface of the housing is coaxial with the axis and extends 360° about the axis, wherein an opening extends through the entire longitudinal length of the cylindrical body, and wherein an opening extends along the entire longitudinal length of the curved inner surface of the housing.

12. The test strip dispenser as set forth in claim 10, wherein the test strip when in the depression and when facing the curved inner surface of the housing engages the curved inner surface of the housing.

13. The test strip dispenser as set forth in claim 10, further comprising a spring member that urges the test strip into the depression, wherein a certain amount of rotation of the cylindrical body about the axis causes the test strip to be moved to a location in which the spring member no longer urges the test strip into the depression.

14. The test strip dispenser as set forth in claim 13, further comprising a top cap that engages the magazine portion and that is removable from the magazine portion, wherein an upper end of the spring member engages the top cap, wherein the top cap and inner walls of the magazine portion define a chamber into which the spring member is located, wherein a plurality of magazine openings are defined through the inner walls of the magazine portion and extend from a location adjacent the top cap towards an end of the magazine portion but terminate short of the end of the magazine portion.

15. The test strip dispenser as set forth in claim 10, wherein a plurality of grates are defined on the outer surface of the cylindrical body.

16. The test strip dispenser as set forth in claim 10, wherein the cylindrical body has an engagement member located on one end and a dial portion located on an opposite end, wherein the body has a flange, wherein the engagement member engages the flange to cause the cylindrical body to be rotatably attached to the housing, wherein the dial portion has a diameter that is larger than the diameter of the outer surface of the cylindrical body, wherein the dial portion has a plurality of grooves thereon and wherein the dial portion is capable of being rotated by the user to cause the cylindrical body to be rotated relative to the housing.

17. The test strip dispenser as set forth in claim 10, wherein a stack of test strips are located in the magazine portion, wherein once the test strip falls out of the depression and through the dispensing opening another one of the test strips from the stack of test strips is available for subsequent placement into the depression;

wherein the housing has a dispensing portion, wherein when the test strip falls through the dispensing opening the test strip subsequently falls through the dispensing portion and out of the test strip dispenser, wherein the test strip falls via gravity out of the depression and through the dispensing opening and out of the test strip dispenser.

18. The test strip dispenser as set forth in claim 10, wherein the depression has a depth of such a size that when the test strip is located in the depression the entire test strip is located at or below the height of surrounding portions of the outer surface of the cylindrical body not located in the depression.

19. A test strip dispenser, comprising:

a housing that has a magazine portion the magazine portion further defining a locking mechanism opening, wherein the housing has a curved inner surface and wherein a dispensing opening extends through the curved inner surface, wherein the housing has a dispensing portion;

a cylindrical body rotatably attached to the housing, wherein the cylindrical body is capable of rotating about an axis such that the cylindrical body rotates relative to the housing, wherein the axis of the cylindrical body is coaxial with an axis of the curved inner surface, wherein the cylindrical body has a dial portion that the user turns in order to effect rotation of the cylindrical body about the axis of the cylindrical body the dial portion defining a notch;

a top cap releasably attached to the top of the magazine portion;

a plurality of test strips stored in the magazine portion wherein the magazine opening extends through the curved inner surface through which a test strip moves from the magazine portion into the depression, wherein the magazine opening and the dispensing opening are positioned 180° from one another about the axis; and a spring member that has a top plate that engages the top cap and that is located within the magazine portion, wherein the spring member has a face plate that engages the plurality of test strips and urges the plurality of test strips away from the top cap;

a locking member that when located within both the notch and the locking mechanism opening effects a locking of the cylindrical body such that the cylindrical body is prevented from rotating about the axis relative to the housing, wherein the locking member is removable from the notch and the locking mechanism opening to effect unlocking of the cylindrical body such that the cylindrical body is capable of rotating about the axis relative to the housing;

wherein a test strip of the plurality of test strips is urged onto an outer surface of the cylindrical body and is subsequently carried by the cylindrical body about the axis of the cylindrical body as the cylindrical body rotates about the axis of the cylindrical body, wherein alignment of the test strip carried by the outer surface of the cylindrical body with the dispensing opening causes the test strip to fall off of and out of engagement with the outer surface of the cylindrical body via gravity and through the dispensing opening and through the dispensing portion and out of the test strip dispenser.

* * * * *